(12) United States Patent
Wachendorff-Neumann et al.

(10) Patent No.: US 8,575,064 B2
(45) Date of Patent: Nov. 5, 2013

(54) SYNERGISTIC FUNGICIDAL ACTIVE SUBSTANCE COMBINATIONS

(75) Inventors: Ulrike Wachendorff-Neumann, Neuwied (DE); Peter Dahmen, Neuss (DE); Ralf Dunkel, Lyons (FR)

(73) Assignee: Bayer CropScience AG, Monheim (DE)

( * ) Notice: Subject to any disclaimer, the term of this patent is extended or adjusted under 35 U.S.C. 154(b) by 950 days.

(21) Appl. No.: 11/910,659

(22) PCT Filed: Mar. 27, 2006

(86) PCT No.: PCT/EP2006/002778
§ 371 (c)(1),
(2), (4) Date: Apr. 15, 2008

(87) PCT Pub. No.: WO2006/105888
PCT Pub. Date: Oct. 12, 2006

(65) Prior Publication Data
US 2010/0273648 A1 Oct. 28, 2010

(30) Foreign Application Priority Data

Apr. 6, 2005 (DE) .................. 10 2005 015 677

(51) Int. Cl.
*A01N 43/56* (2006.01)
*A01N 43/653* (2006.01)
(52) U.S. Cl.
USPC ............................. 504/100; 514/383; 514/406
(58) Field of Classification Search
USPC ................................. 514/383, 406; 504/100
See application file for complete search history.

(56) References Cited

U.S. PATENT DOCUMENTS

| | | | |
|---|---|---|---|
| 1,972,961 A | 9/1934 | Tisdale et al. |
| 2,504,404 A | 4/1950 | Flenner |
| 2,553,770 A | 5/1951 | Kittleson et al. |
| 2,588,428 A | 3/1952 | Stewart et al. |
| 3,010,968 A | 11/1961 | Loux et al. |
| 3,178,447 A | 4/1965 | Kohn et al. |
| 3,206,468 A | 9/1965 | Grenda et al. |
| 3,248,400 A | 4/1966 | Flieg et al. |
| 3,249,499 A | 5/1966 | von Schmeling et al. |
| 3,285,929 A | 11/1966 | Klauke et al. |
| 3,379,610 A | 4/1968 | Lyon et al. |
| 3,499,951 A | 3/1970 | Schrader et al. |
| 3,513,241 A | 5/1970 | Hoyer et al. |
| 3,546,813 A | 12/1970 | Frohberger et al. |
| 3,629,428 A | 12/1971 | Seki et al. |
| 3,631,176 A | 12/1971 | Klopping et al. |
| 3,745,170 A | 7/1973 | Fujinami et al. |
| 3,745,187 A | 7/1973 | Noguchi et al. |
| 3,755,350 A | 8/1973 | Sauli |
| 3,856,814 A | 12/1974 | Taninaka et al. |
| 3,912,752 A | 10/1975 | Meiser et al. |
| 3,952,002 A | 4/1976 | Kramer et al. |
| 3,966,750 A | 6/1976 | Mangold et al. |
| 3,991,071 A | 11/1976 | Brookes et al. |
| 4,046,911 A | 9/1977 | Hubele |
| 4,068,077 A | 1/1978 | Goetz et al. |
| 4,079,062 A | 3/1978 | Van Reet et al. |
| 4,127,673 A | 11/1978 | Yamada et al. |
| 4,239,760 A | 12/1980 | Sasse et al. |
| 4,245,432 A | 1/1981 | Dannelly |
| 4,272,417 A | 6/1981 | Barke et al. |
| 4,291,049 A | 9/1981 | Bosone et al. |
| 4,432,989 A | 2/1984 | Spencer |
| 4,496,551 A | 1/1985 | Moberg |
| 4,532,341 A | 7/1985 | Holmwood et al. |
| 4,551,469 A | 11/1985 | Parry et al. |
| 4,598,085 A | 7/1986 | Heeres et al. |
| 4,652,580 A | 3/1987 | Janssen et al. |
| 4,659,739 A | 4/1987 | Yoshioka et al. |
| 4,664,696 A | 5/1987 | Schaub |
| 4,723,984 A * | 2/1988 | Holmwood et al. .......... 504/272 |
| 4,731,106 A | 3/1988 | Green et al. |
| 4,808,430 A | 2/1989 | Kouno |

(Continued)

FOREIGN PATENT DOCUMENTS

AU 610079 B2 5/1991
DE 140 0 41 A 2/1980

(Continued)

OTHER PUBLICATIONS

Tomiya et al., The BCPC International Congress—Crop Science & Technology 2003, vol. 1, pp. 99-104 (2003).*
Machine translation of JP 2001-72512 (Mar. 21, 2001).*
Derwent abstract 2001-412291; abstracting JP 2001-72512 (Mar. 21, 2001).*
HCAPLUS abstract 2004:412291 (2001).*
Bauer, T.A., et al., "Response of Selected Weed Species to Postemergence Imazethapyr and Bentazon," *Weed Tech.* 9:236-242, The Weed Science Society of America, United States (1995).
Blackshaw, R.E., "HOE-39866 Use in Chemical Fallow Systems," *Weed Tech.* 3:420-428, The Weed Science Society of America, United States (1989).
Blackshaw, R.E., "Synergistic Mixes of DPX-A7881 and Clopyralid in Canola (*Brassica napus*)," *Weed Tech.* 3:690-695, The Weed Science Society of America, United States (1989).

(Continued)

*Primary Examiner* — John Pak
(74) *Attorney, Agent, or Firm* — Sterne, Kessler, Goldstein & Fox, P.L.L.C.

(57) ABSTRACT

The novel active compound combinations of a carboxamide of the general formula (I) (group 1)

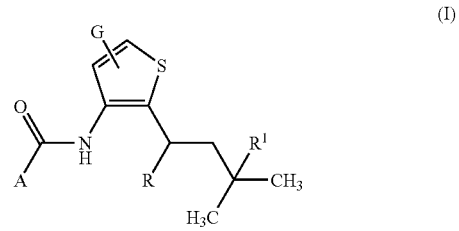

(I)

in which R, G, R¹ and A have the meanings given in the description
and the active compound groups (2) to (23) listed in the description have very good fungicidal properties.

29 Claims, No Drawings

(56) References Cited

U.S. PATENT DOCUMENTS

| | | |
|---|---|---|
| 4,840,959 A | 6/1989 | Oda et al. |
| 4,851,405 A | 7/1989 | Kramer et al. |
| 4,877,441 A | 10/1989 | Mori et al. |
| 4,902,705 A | 2/1990 | Hirota et al. |
| 4,920,139 A | 4/1990 | Fujimoto |
| 4,931,560 A | 6/1990 | Hubele |
| 4,931,581 A | 6/1990 | Schurter et al. |
| 4,988,734 A | 1/1991 | Kraatz et al. |
| 4,995,898 A | 2/1991 | Nasu et al. |
| 5,021,581 A | 6/1991 | Clough et al. |
| 5,059,623 A | 10/1991 | Krüger et al. |
| 5,081,141 A | 1/1992 | Colle et al. |
| 5,087,635 A | 2/1992 | Shaber |
| 5,112,849 A | 5/1992 | Staub et al. |
| 5,145,843 A | 9/1992 | Arnold et al. |
| 5,145,856 A | 9/1992 | Clough et al. |
| 5,185,342 A | 2/1993 | Hayase et al. |
| 5,221,691 A | 6/1993 | Clough et al. |
| 5,254,584 A | 10/1993 | Michelotti et al. |
| 5,256,683 A | 10/1993 | Hutt et al. |
| 5,266,585 A | 11/1993 | Hubele et al. |
| 5,304,523 A | 4/1994 | Michelotti et al. |
| 5,306,712 A | 4/1994 | Tobitsuka et al. |
| 5,334,607 A | 8/1994 | Sauter et al. |
| 5,407,902 A | 4/1995 | Oda et al. |
| 5,453,531 A | 9/1995 | Seitz et al. |
| 5,486,621 A | 1/1996 | Phillion et al. |
| 5,514,643 A | 5/1996 | Rew et al. |
| 5,578,725 A | 11/1996 | Portoghese et al. |
| 5,593,996 A | 1/1997 | Pees et al. |
| 5,637,729 A | 6/1997 | Lacroix et al. |
| 5,679,676 A | 10/1997 | Krüger et al. |
| 5,747,497 A | 5/1998 | Bereznak et al. |
| 5,747,518 A * | 5/1998 | Yoshikawa et al. ............ 514/403 |
| 5,789,428 A | 8/1998 | Shibata et al. |
| 5,789,430 A | 8/1998 | Jautelat et al. |
| 5,859,039 A | 1/1999 | Jautelat et al. |
| 5,869,517 A | 2/1999 | Müller et al. |
| 5,876,739 A | 3/1999 | Turnblad et al. |
| 5,922,905 A | 7/1999 | Curtze et al. |
| 5,948,932 A | 9/1999 | Grote et al. |
| 5,986,135 A | 11/1999 | Pfrengle et al. |
| 5,998,455 A | 12/1999 | Knauf-Beiter et al. |
| 6,103,717 A | 8/2000 | Heinemann et al. |
| 6,114,362 A | 9/2000 | Dutzmann et al. |
| 6,277,858 B1 | 8/2001 | Walter |
| 6,297,263 B1 | 10/2001 | Dutzmann et al. |
| 6,306,850 B1 | 10/2001 | Dutzmann et al. |
| 6,355,634 B1 | 3/2002 | Isenring et al. |
| 6,407,100 B1 | 6/2002 | Isenring et al. |
| 6,423,726 B2 | 7/2002 | Dutzmann et al. |
| 6,616,054 B1 | 9/2003 | Norton |
| 6,683,211 B1 | 1/2004 | Lamberth et al. |
| 7,008,903 B2 | 3/2006 | Dutzmann et al. |
| 7,884,049 B2 | 2/2011 | Dutzmann et al. |
| 2001/0018442 A1 | 8/2001 | Gayer et al. |
| 2002/0091067 A1 | 7/2002 | Assmann et al. |
| 2002/0115564 A1 | 8/2002 | Asrar et al. |
| 2002/0134012 A1 | 9/2002 | Ding et al. |
| 2002/0173529 A1 | 11/2002 | Dutzmann et al. |
| 2002/0198222 A1 | 12/2002 | Bruns et al. |
| 2003/0027842 A1 | 2/2003 | Assmann et al. |
| 2003/0171410 A1 | 9/2003 | Moloney et al. |
| 2003/0176428 A1 | 9/2003 | Schneidersmann et al. |
| 2004/0110771 A1 | 6/2004 | Blasco et al. |
| 2004/0192672 A1 | 9/2004 | Wegmann et al. |
| 2005/0101639 A1 | 5/2005 | Ammermann et al. |
| 2006/0004070 A1 | 1/2006 | Wachendorff-Neumann et al. |
| 2006/0079401 A1 | 4/2006 | Dutzmann et al. |
| 2008/0269051 A1 | 10/2008 | Suty-Heinze et al. |
| 2008/0312184 A1 | 12/2008 | Inami et al. |
| 2009/0286681 A1 | 11/2009 | Dahmen et al. |
| 2009/0306109 A1 | 12/2009 | Dutzmann et al. |
| 2010/0041659 A1 | 2/2010 | Dutzmann et al. |
| 2011/0003869 A1 | 1/2011 | Wetcholowsky et al. |

FOREIGN PATENT DOCUMENTS

| | | |
|---|---|---|
| DE | 30 30 026 A1 | 3/1981 |
| DE | 1 151 404 A | 10/1981 |
| EP | 0 258 161 A2 | 3/1988 |
| EP | 0 262 393 A1 | 4/1988 |
| EP | 0 329 397 A1 | 8/1989 |
| EP | 0 393 911 A1 | 10/1990 |
| GB | 935981 | 9/1963 |
| GB | 988630 | 4/1965 |
| GB | 1094567 | 12/1967 |
| GB | 1103989 | 2/1968 |
| GB | 1 114155 | 5/1968 |
| GB | 1 591 267 | 6/1981 |
| JP | 7-206608 A | 8/1995 |
| JP | 11-228309 A | 8/1999 |
| JP | 11-292715 A | 10/1999 |
| JP | 11-302107 A | 11/1999 |
| JP | 11-302108 A | 11/1999 |
| JP | 11-302109 A | 11/1999 |
| JP | 11-302110 A | 11/1999 |
| JP | 11-302111 A | 11/1999 |
| JP | 11-322513 A | 11/1999 |
| JP | 11-322514 A | 11/1999 |
| JP | 2001-72512 * | 3/2001 |
| JP | 2001-72513 A | 3/2001 |
| WO | WO 98/23155 A | 6/1998 |
| WO | WO 2006/036827 * | 4/2006 |
| WO | WO 2006/082723 A1 | 8/2006 |

OTHER PUBLICATIONS

Blackshaw, R.E., et al., "Herbicide Combinations for Postemergent Weed Control in Safflower (*Carthamus tinctorius*)," Weed Tech. 4:97-104, The Weed Science Society of America, United States (1990).

Blouin, D.C., et al., "Analysis of Synergistic and Antagonistic Effects of Herbicides Using Nonlinear Mixed-Model Methodology," Weed Tech. 18:464-472, The Weed Science Society of America, United States (2004).

Bradley, P.R., et al., "Response of Sorghum (*Sorghum bicolor*) to Atrazine, Ammonium Sulfate, and Glyphosate," Weed Tech. 14:15-18, The Weed Science Society of America, United States (2000).

Buker, III, R.S., et al., "Confirmation and Control of a Paraquat-Tolerant Goosegrass (*Eleusine indica*) Biotype," Weed Tech. 16:309-313, The Weed Science Society of America, United States (2002).

Burke, I.C., et al., "CGA-362622 Antagonizes Annual Grass Control with Clethodim," Weed Tech. 16:749-754, The Weed Science Society of America, United States (2002).

Flint, J.L., et al., "Analyzing Herbicide Interactions, A Statistical Treatment of Colby's Method," Weed Tech. 2:304-309, The Weed Science Society of America, United States (1988).

Gillespie, G.R., and Nalewaja, J.D., "Wheat (*Triticum aestivum*) Response to Triallate Plus Chlorsulfuron," Weed Tech. 3:20-23, The Weed Science Society of America, United States (1989).

Green, J.M., et al., "Metribuzin and Chlorimuron Mixtures for Preemergence Broadleaf Weed Control in Soybeans, *Glycine max*," Weed Tech. 2:355-363, The Weed Science Society of America, United States (1988).

Harker, N.K., and O'Sullivan, P.A., "Synergistic Mixtures of Sethoxydim and Fluazifop on Annual Grass Weeds," Weed Tech. 5:310-316, The Weed Science Society of America, United States (1991).

Kent, L.M., et al., "Effect of Ammonium Sulfate, Imazapyr, and Environment on the Phytotoxicity of Imazethapyr," Weed Tech. 5:202-205, The Weed Science Society of America, United States (1991).

Kotoula-Syka, E., et al., "Interactions between SAN 582H and Selected Safeners on Grain Sorghum (*Sorghum bicolor*) and Corn (*Zea mays*)," Weed Tech. 10:299-304, The Weed Science Society of America, United States (1996).

Lanclos, D.Y., et al., "Glufosinate Tank-Mix Combinations in Glufosinate-Resistant Rice (*Oryza sativa*)," Weed Tech. 16:659-663, The Weed Science Society of America, United States (2002).

Norris, J.L., et al., "Weed Control from Herbicide Combinations with Three Formulations of Glyphosate," Weed Tech. 15:552-558, The Weed Science Society of America, United States (2001).

(56) References Cited

OTHER PUBLICATIONS

Novosel, K.M., et al., "Metolachlor Efficacy as Influenced by Three Acetolactate Synthase-Inhibiting Herbicides," *Weed Tech.* 12:248-253, The Weed Science Society of America, United States (1998).
Palmer, E.W., et al., "Broadleaf Weed Control in Soybean (*Glycine max*) with CGA-277476 and Four Postemergence Herbicides," *Weed Tech.* 14:617-623, The Weed Science Society of America, United States (2000).
Salzman, F.P., and Renner, K.A., "Response of Soybean Combinations of Clomazone, Metribuzin, Linuron, Alachlor, and Atrazine," *Weed Tech.* 6:922-929, The Weed Science Society of America, United States (1992).
Scott, R.C., et al., "Spray Adjuvant, Formulation, and Environmental Effects of Synergism from Post-Applied Tank Mixtures of SAN 582H with Fluazifop-P, Imazethapyr, and Sethoxydim," *Weed Tech.* 12:463-469, The Weed Science Society of America, United States (1998).
Shaw, D.R. and Arnold, J.C., "Weed Control from Herbicide Combinations with Glyphosate," *Weed Tech.* 16:1-6, The Weed Science Society of America, United States (2002).
Snipes, C.E., and Allen, R.L., "Interaction of Graminicides Applied in Combination with Pyrithiobac," *Weed Tech.* 10:889-892, The Weed Science Society of America, United States (1996).
Wehtje, G. and Walker, R.H., "Interaction of Glyphosate and 2,4-DB for the Control of Selected Morningglory (*Ipomoea* spp.) Species," *Weed Tech.* 11:152-156, The Weed Science Society of America, United States (1997).
Zhang, W., et al., "Fenoxaprop Interactions for Barnyardgrass (*Echinochloa crus-galli*) Control in Rice," *Weed Tech.* 19:293-297, The Weed Science Society of America, United States (2005).
Rummens, F.H.A., "An Improved Definition of Synergistic and Antagonistic Effects," *Weed Science* 23(1):4-6, The Weed Science Society of America, United States (1975).
Tomlin, C., ed., *The Pesticide Manual*, 1242-1245, British Crop Protection Council, Farnham, UK (1997).
Partial English language translation of Prosecution History of European Patent Appl. No. 03735610.2, Jul. 13, 2006-Sep. 25, 2009.
Opposition Proceeding in European Patent No. EP-B-1482798, Mar. 5, 2007-Nov. 9, 2009.
Partial English language translation of Opposition Proceeding in European Patent No. EP-B-1482798, Feb. 26, 2007-Nov. 9, 2009.
"Azoxystrobin data sheet," Compendium of Pesticide Common Names, accessed accessed at http://www.alanwood.net/pesticides/azoxystrobin.html, accessed on Apr. 8, 2009, 1 page.
"Kresoxim-methyl data sheet," Compendium of Pesticide Common Names, accessed at http://www.alanwood.net/pesticides/kresoxim-methyl.html, accessed on Apr. 8, 2009, 1 page.
"Metominostrobin data sheet," Compendium of Pesticide Common Names, accessed at http://www.alanwood.net/pesticides/metominostrobin.html, accessed on Apr. 8, 2009, 1 page.
English language Abstract of Japanese Application No. JP 11-228309 A, European Patent Office, espacenet database—worldwide, (2001).
English language Abstract of Japanses Application No. JP 2001-72513 A, European Patent Office, espacenet database—worldwide, (2001).
English language Translation of Japanese Office Action in Japanese Application No. JP 2008-504660, mailed Oct. 18, 2011.
Colby, S.R., "Calculating Synergistic and Antagonistic Responses of Herbicide Combinations," *Weeds* 15:20-22 (1967).
Pesticide Manual 1991, pp. 249 and 827.
Dialog File 351, Accession No. 1929188, Derwent WPI English language abstract for DD 140 0 41 A (listed as document FP6 on the accompanying form PTO/SB/08A), 1980.
Dialog File 351, Accession No. 2335546, Derwent WPI English language abstract for DE 30 30 026 A1 (listed as document FP7 on the accompanying form PTO/SB/08A), 1981.
Dialog File 351, Accession No. 2357635, Derwent WPI English language abstract for DD 1 511 404 A (listed as document FP9 on the accompanying form PTO/SB/08A), 1981
Dialog File 351, Accession No. 4328299, Derwent WPI English language abstract for EP 0 258 161 A2 (listed as document FP10 on the accompanying form PTO/SB/08A), 1988.
Dialog File 351, Accession No. 4359877, Derwent WPI English language abstract for EP 0 262 393 A1 (listed as document FP11 on the accompanying form PTO/SB/08A), 1988.
Dialog File 351, Accession No. 7254716, Derwent WPI English language abstract for JP 7-206608 A (listed as document FP14 on the accompanying form PTO/SB/08A), 1995.
Dialog File 351, Accession No. 9733319, Derwent WPI English language abstract for JP 11-292715 A (listed as document FP16 on the accompanying form PTO/SB/08A), 1999.
Dialog File 351, Accession No. 9786483, Derwent WPI English language abstract for JP 11-302107 A (listed as document FP17 on the accompanying form PTO/SB/08A), 1999.
Dialog File 351, Accession No. 9786484, Derwent WPI English language abstract for JP 11-302108 A (listed as document FP18 on the accompanying form PTO/SB/08A), 1999.
Dialog File 351, Accession No. 9786485, Derwent WPI English language abstract for JP 11-302109 A (listed as document FP19 on the accompanying form PTO/SB/08A), 1999.
Dialog File 351, Accession No. 9786486, Derwent WPI English language abstract for JP 11-302110 A (listed as document FP20 on the accompanying form PTO/SB/08A), 1999.
Dialog File 351, Accession No. 9786487, Derwent WPI English language abstract for JP 11-302111 A (listed as document FP21 on the Accompanying form PTO/SB/08A), 1999.
Dialog File 351, Accession No. 9780664, Derwent WPI English language abstract for JP 11-322513 A (listed as document FP22 on the accompanying form PTO/SB/08A), 1999.
Dialog File 351, Accession No. 9780665, Derwent WPI English language abstract for JP 11-322514 A (listed as document FP23 on the accompanying form PTO/SB/08A), 1999.
International Search Report for International Application No. PCT/EP2006/002778, European Patent Office, Netherlands, mailed on Dec. 18, 2006.

* cited by examiner

SYNERGISTIC FUNGICIDAL ACTIVE SUBSTANCE COMBINATIONS

This application is a National Stage of International Application No. PCT/EP2006/002778, filed Mar. 27, 2006, which claims the benefit of German Patent Application No. 102005015677.0, filed Apr. 6, 2005. The entirety of each of these applications is incorporated by reference herein.

The present invention relates to novel active compound combinations comprising, firstly, known carboxamides and, secondly, further known fungicidally active compounds, which combinations are highly suitable for controlling unwanted phytopathogenic fungi.

It is already known that certain carboxamides have fungicidal properties: for example N-[2-(1,3-dimethylbutyl)-3-thienyl]-1-methyl-3-(trifluoromethyl)-1H-pyrazole-4-carboxamide from EP-A 0 737 682. The activity of these compounds is good; however, at low application rates it is sometimes unsatisfactory. Furthermore, it is already known that numerous triazole derivatives, aniline derivatives, dicarboximides and other heterocycles can be used for controlling fungi (cf. EP-A 0 040 345, DE-A 22 01 063, DE-A 23 24 010, Pesticide Manual, 9th Edition (1991), pages 249 and 827, EP-A 0 382 375 and EP-A 0 515 901). However, the activity of these compounds, too, is not always sufficient at low application rates. Furthermore, it is already known that 1-(3,5-dimethylisoxazole-4-sulfonyl)-2-chloro-6,6-difluoro-[1,3]-dioxolo-[4,5f]-benzimidazole has fungicidal properties (cf. WO 97/06171). Finally, it is also known that substituted halopyrimidines have fungicidal properties (cf. DE-A1-196 46 407, EP-B-712 396).

Also known are various mixtures of alkylthienylcarboxamides. The activity of these mixtures, too, is sometimes unsatisfactory (cf. JP-A 11-292715, JP-A 11-302107, JP-A 11-302108, JP-A 11-302109, JP-A 11-302110, JP-A 11-302111, JP-A 2001-72511, JP-A 2001-72512, JP-A 2001-72513, JP-A 11-322513, JP-A 11-322514, JP-A 2000-53506 and JP-A 2000-53507).

This invention now provides novel active compound combinations which have very good fungicidal properties and comprise a carboxamide of the general formula (I) (group 1)

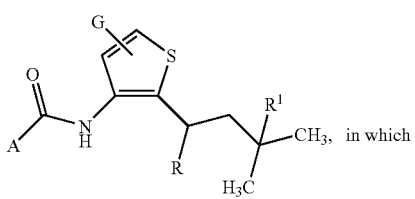

(I)

in which

R represents hydrogen or methyl,
G represents hydrogen, fluorine or methyl,
R$^1$ represents hydrogen, halogen, C$_1$-C$_3$-alkyl or C$_1$-C$_3$-haloalkyl having 1 to 7 fluorine, chlorine and/or bromine atoms, A represents one of the radicals A1 or A2 below:

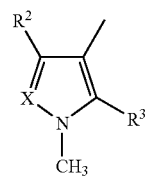

A1

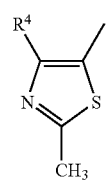

A2

X represents CH or N,
R$^2$ represents methyl, difluoromethyl or trifluoromethyl,
R$^3$ represents hydrogen or fluorine,
R$^4$ represents difluoromethyl or trifluoromethyl,
and at least one active compound selected from groups (2) to (23) below:
Group (2) Strobilurins
(2-1) fluoxastrobin (known from DE-A 196 02 095) of the formula

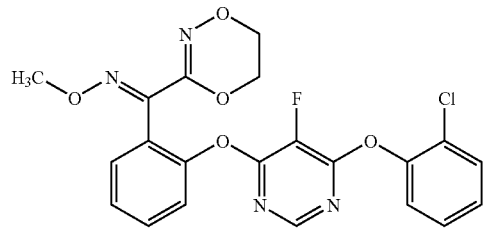 [SMILES: CO/N=C(/C1=NOCCO1)c1ccccc1Oc1ncnc(Oc2ccccc2Cl)c1F]

(2-2) (2E)-2-(2-{[6-(3-chloro-2-methylphenoxy)-5-fluoro-4-pyrimidinyl]oxy}phenyl)-2-(methoxyimino)-N-methylethanamide (known from DE-A 196 46 407, EP-B 0 712 396) of the formula

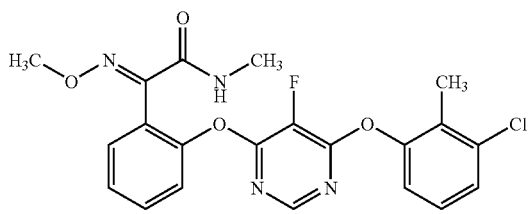 [SMILES: CNC(=O)/C(=N/OC)c1ccccc1Oc1ncnc(Oc2cccc(Cl)c2C)c1F]

(2-3) trifloxystrobin (known from EP-A 0 460 575) of the formula

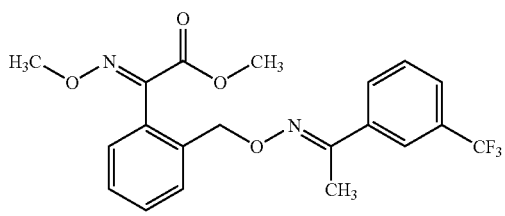 [SMILES: CO/N=C(/C(=O)OC)c1ccccc1CO/N=C(\C)c1cccc(C(F)(F)F)c1]

(2-4) (2E)-2-(methoxyimino)-N-methyl-2-(2-{[({(1E)-1-[3-(trifluoromethyl)phenyl]ethylidene}-amino)oxy]methyl}phenyl)ethanamide (known from EP-A 0 569 384) of the formula

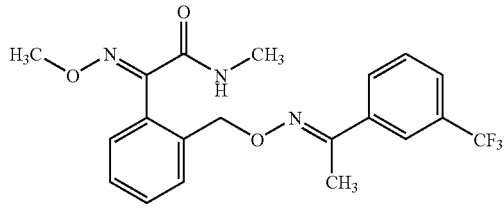 [SMILES: CNC(=O)/C(=N/OC)c1ccccc1CO/N=C(\C)c1cccc(C(F)(F)F)c1]

(2-5) (2E)-2-(methoxyimino)-N-methyl-2-{2-[(E)-({1-[3-(trifluoromethyl)phenyl]ethoxy}imino)-methyl]phenyl}ethanamide (known from EP-A 0 596 254) of the formula

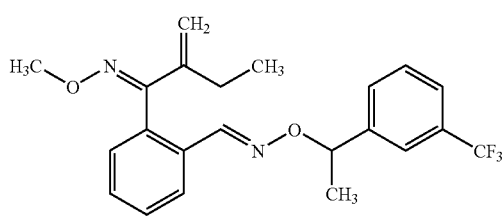 [SMILES: C=C(CC)/C(=N/OC)c1ccccc1/C=N/OC(C)c1cccc(C(F)(F)F)c1]

(2-6) orysastrobin (known from DE-A 195 39 324) of the formula

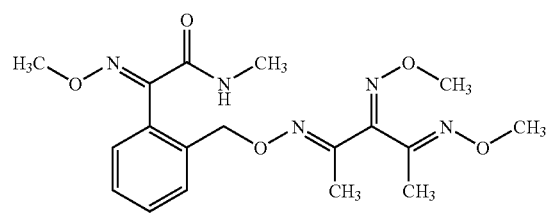

(2-7) 5-methoxy-2-methyl-4-(2-{[({(1E)-1-[3-(trifluoromethyl)phenyl]ethylidene}amino)oxy]-methyl}phenyl)-2,4-dihydro-3H-1,2,4-triazol-3-one (known from WO 98/23155) of the formula

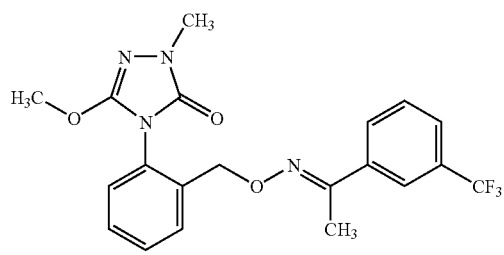 [SMILES: COc1nn(C)c(=O)n1-c1ccccc1CO/N=C(\C)c1cccc(C(F)(F)F)c1]

(2-8) dimoxystrobin (known from EP-A 0 398 692) of the formula

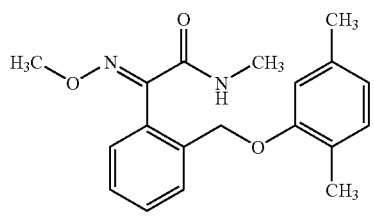 [SMILES: CNC(=O)/C(=N/OC)c1ccccc1COc1cc(C)ccc1C]

(2-9) picoxystrobin (known from EP-A 0 278 595) of the formula

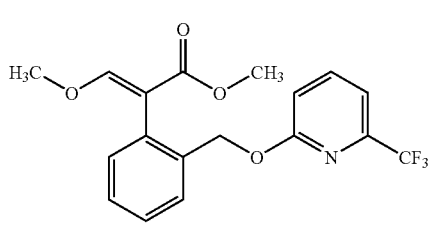 [SMILES: CO/C=C(/C(=O)OC)c1ccccc1COc1cccc(C(F)(F)F)n1]

(2-10) pyraclostrobin (known from DE-A 44 23 612) of the formula

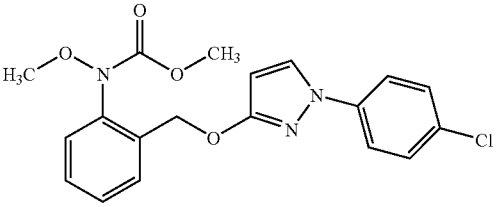 [SMILES: COC(=O)N(OC)c1ccccc1COc1ccn(-c2ccc(Cl)cc2)n1]

Group (3) Triazoles
(3-1) azaconazole (known from DE-A 25 51 560) of the formula

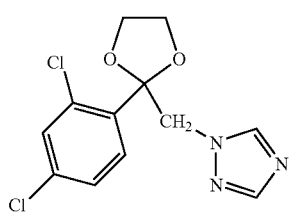 [SMILES: Clc1ccc(C2(Cn3cncn3)OCCO2)c(Cl)c1]

(3-2) etaconazole (known from DE-A 25 51 560) of the formula

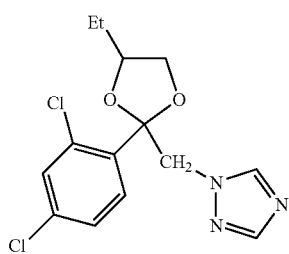 [SMILES: CCC1COC(Cn2cncn2)(c2ccc(Cl)cc2Cl)O1]

(3-3) propiconazole (known from DE-A 25 51 560) of the formula

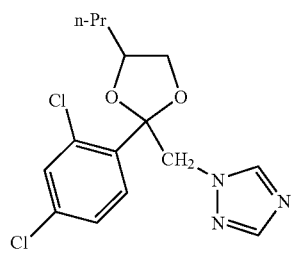

(3-4) difenoconazole (known from EP-A 0 112 284) of the formula

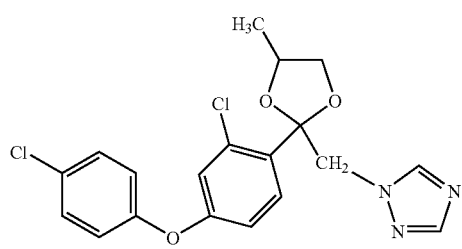 [SMILES: CC1COC(Cn2cncn2)(c2ccc(Oc3ccc(Cl)cc3)cc2Cl)O1]

(3-5) bromuconazole (known from EP-A 0 258 161) of the formula

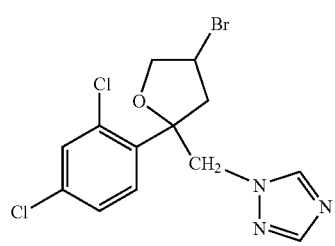 [SMILES: Clc1ccc(C2(Cn3cncn3)CC(Br)CO2)c(Cl)c1]

(3-6) cyproconazole (known from DE-A 34 06 993) of the formula

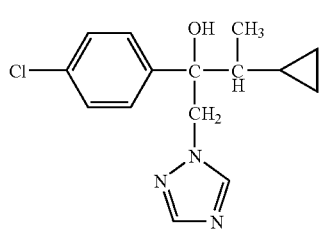 [SMILES: CC(C1CC1)C(O)(Cn1cncn1)c1ccc(Cl)cc1]

(3-7) hexaconazole (known from DE-A 30 42 303) of the formula

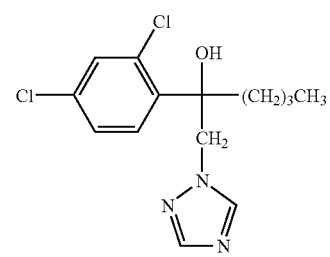

(3-8) penconazole (known from DE-A 27 35 872) of the formula

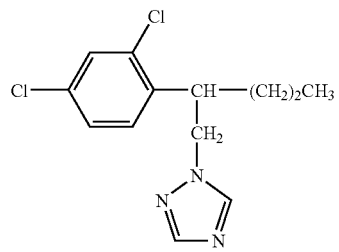

(3-9) myclobutanil (known from EP-A 0 145 294) of the formula

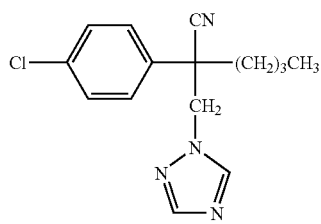

(3-10) tetraconazole (known from EP-A 0 234 242) of the formula

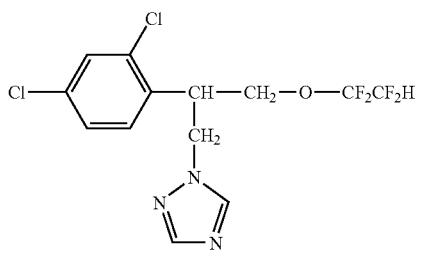

(3-11) flutriafol (known from EP-A 0 015 756) of the formula

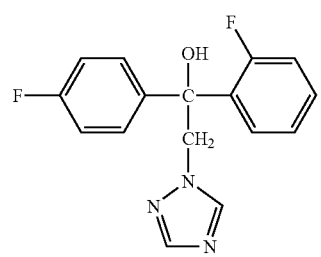 [SMILES: OC(Cn1cncn1)(c1ccc(F)cc1)c1ccccc1F]

(3-12) epoxiconazole (known from EP-A 0 196 038) of the formula

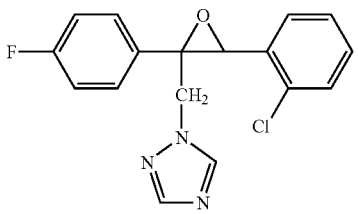 [SMILES: Fc1ccc(C2(Cn3cncn3)OC2c2ccccc2Cl)cc1]

(3-13) flusilazole (known from EP-A 0 068 813) of the formula

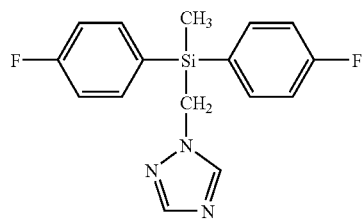 [SMILES: C[Si](Cn1cncn1)(c1ccc(F)cc1)c1ccc(F)cc1]

(3-14) simeconazole (known from EP-A 0 537 957) of the formula

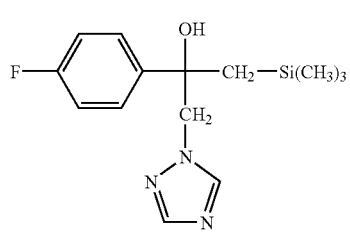

(3-15) prothioconazole (known from WO 96/16048) of the formula

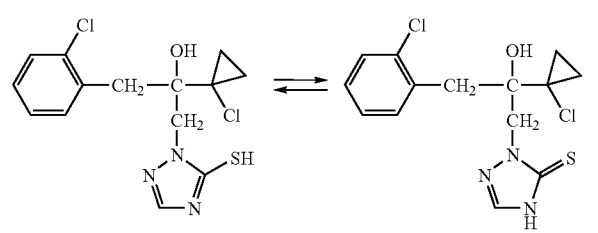 [SMILES: OC(Cc1ccccc1Cl)(Cn1ncnc1S)C1(Cl)CC1 ; OC(Cc1ccccc1Cl)(Cn1nc[nH]c1=S)C1(Cl)CC1]

(3-16) fenbuconazole (known from DE-A 37 21 786) of the formula

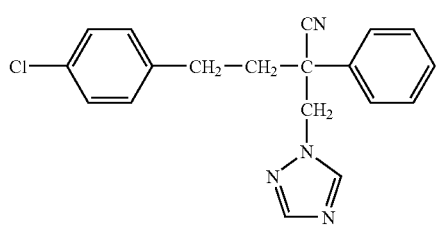 [SMILES: N#CC(CCc1ccc(Cl)cc1)(Cn1cncn1)c1ccccc1]

(3-17) tebuconazole (known from EP-A 0 040 345) of the formula

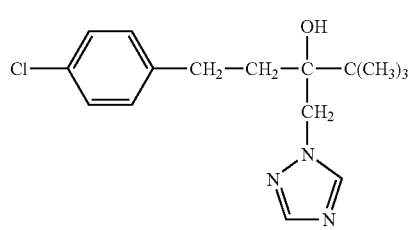 [SMILES: CC(C)(C)C(O)(CCc1ccc(Cl)cc1)Cn1cncn1]

(3-18) ipconazole (known from EP-A 0 329 397) of the formula

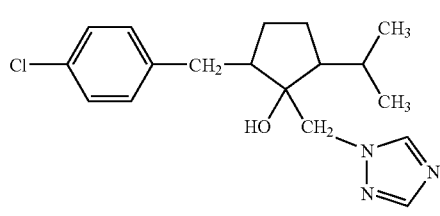 [SMILES: CC(C)C1CCC(Cc2ccc(Cl)cc2)C1(O)Cn1cncn1]

(3-19) metconazole (known from EP-A 0 329 397) of the formula

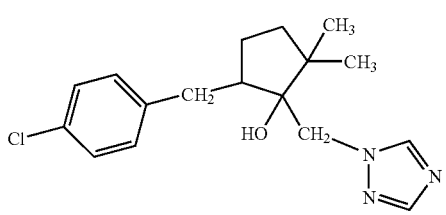 [SMILES: CC1(C)CCC(Cc2ccc(Cl)cc2)C1(O)Cn1cncn1]

(3-20) triticonazole (known from EP-A 0 378 953) of the formula

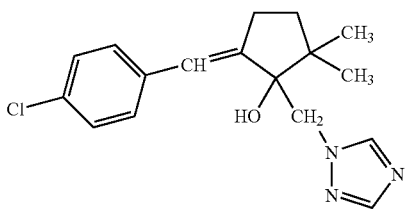 [SMILES: CC1(C)CC/C(=C/c2ccc(Cl)cc2)C1(O)Cn1cncn1]

(3-21) bitertanol (known from DE-A 23 24 010) of the formula

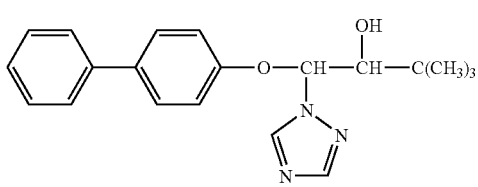 [SMILES: CC(C)(C)C(O)C(Oc1ccc(-c2ccccc2)cc1)n1cncn1]

(3-22) triadimenol (known from DE-A 23 24 010) of the formula

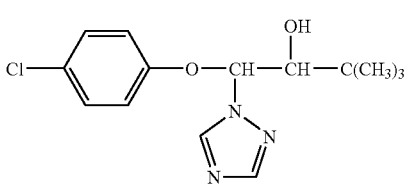 [SMILES: CC(C)(C)C(O)C(Oc1ccc(Cl)cc1)n1cncn1]

(3-23) triadimefon (known from DE-A 22 01 063) of the formula

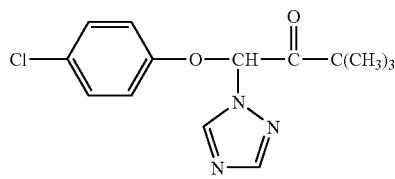 [SMILES: CC(C)(C)C(=O)C(Oc1ccc(Cl)cc1)n1cncn1]

(3-24) fluquinconazole (known from EP-A 0 183 458) of the formula

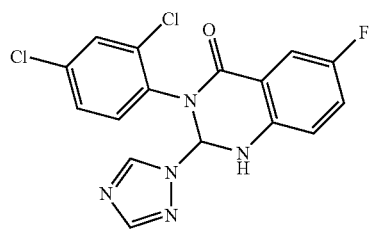 [SMILES: O=C1c2cc(F)ccc2NC(n2cncn2)N1c1ccc(Cl)cc1Cl]

(3-25) quinconazole (known from EP-A 0 183 458) of the formula

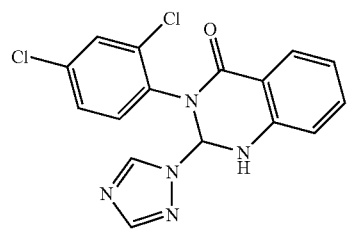 [SMILES: O=C1c2ccccc2NC(n2cncn2)N1c1ccc(Cl)cc1Cl]

Group (4) Sulfenamides (4-1) dichlofluanid (known from DE-A 11 93 498) of the formula

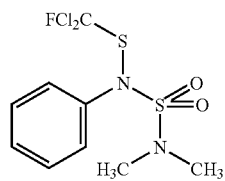

(4-2) tolylfluanid (known from DE-A 11 93 498) of the formula

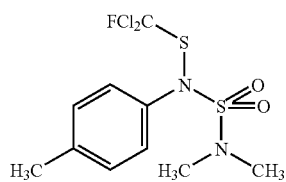

Group (5) Valinamides (5-1) iprovalicarb (known from DE-A 40 26 966) of the formula

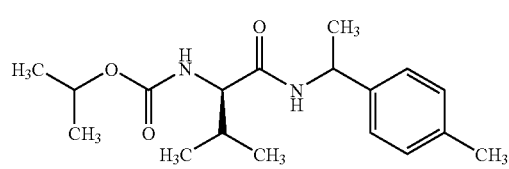 [SMILES: Cc1ccc(C(C)NC(=O)[C@H](NC(=O)OC(C)C)C(C)C)cc1]

(5-2) benthiavalicarb (known from WO 96/04252) of the formula

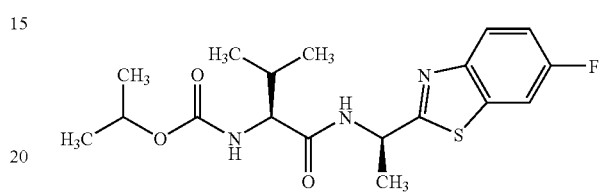

Group (6) Carboxamides (6-1) 2-chloro-N-(1,1,3-trimethylindan-4-yl)nicotinamide (known from EP-A 0 256 503) of the formula

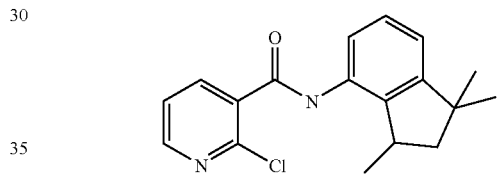

(6-2) boscalid (known from DE-A 195 31 813) of the formula

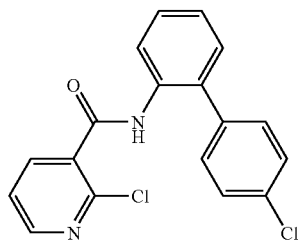 [SMILES: O=C(Nc1ccccc1-c1ccc(Cl)cc1)c1cccnc1Cl]

(6-3) furametpyr (known from EP-A 0 315 502) of the formula

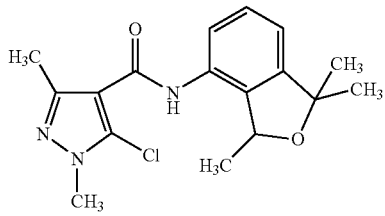

(6-4) ethaboxam (known from EP-A 0 639 574) of the formula

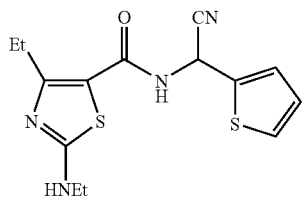

(6-5) fenhexamid (known from EP-A 0 339 418) of the formula

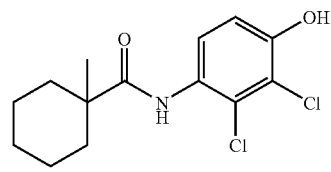 [SMILES: CC1(C(=O)Nc2ccc(O)c(Cl)c2Cl)CCCCC1]

(6-6) carpropamid (known from EP-A 0 341 475) of the formula

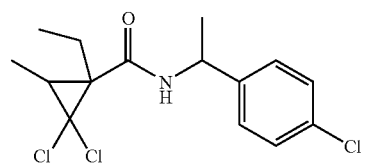 [SMILES: CCC1(C(=O)NC(C)c2ccc(Cl)cc2)C(C)C1(Cl)Cl]

(6-7) 2-chloro-4-(2-fluoro-2-methylpropionylamino)-N,N-dimethylbenzamide (known from EP-A 0 600 629) of the formula

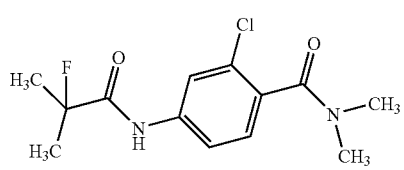 [SMILES: CN(C)C(=O)c1ccc(NC(=O)C(C)(C)F)cc1Cl]

(6-8) picobenzamid (known from WO 99/42447) of the formula

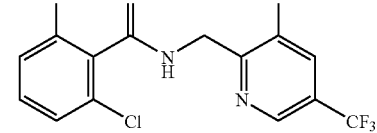

(6-9) zoxamide (known from EP-A 0 604 019) of the formula

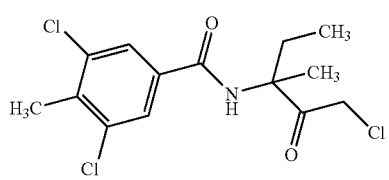 [SMILES: CCC(C)(NC(=O)c1cc(Cl)c(C)c(Cl)c1)C(=O)CCl]

(6-10) 3,4-dichloro-N-(2-cyanophenyl)isothiazole-5-carboxamide (known from WO 99/24413) of the formula

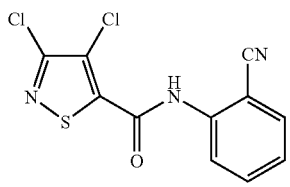 [SMILES: N#Cc1ccccc1NC(=O)c1snc(Cl)c1Cl]

(6-11) carboxin (known from U.S. Pat. No. 3,249,499) of the formula

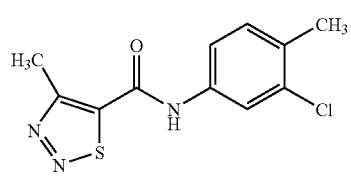 [SMILES: Cc1ccc(NC(=O)c2snnc2C)cc1Cl]

(6-12) tiadinil (known from U.S. Pat. No. 6,616,054) of the formula

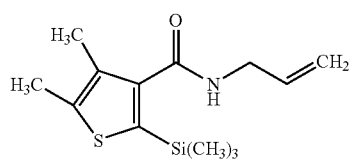

(6-13) silthiofam (known from WO 96/18631) of the formula

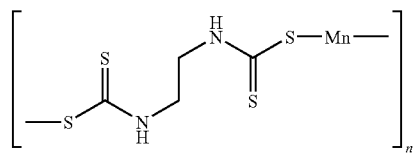

Group (7) Dithiocarbamates (7-1) mancozeb (known from DE-A 12 34 704) having the IUPAC name Manganese ethylenebis(dithiocarbamate) (polymeric) complex with zinc salt (7-2) maneb (known from U.S. Pat. No. 2,504,404) of the formula

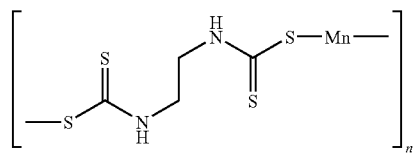

(7-3) metiram (known from DE-A 10 76 434) having the IUPAC name Zinc ammoniate ethylenebis(dithiocarbamate)-poly(ethylenethiuram disulfide)

(7-4) propineb (known from GB 935 981) of the formula

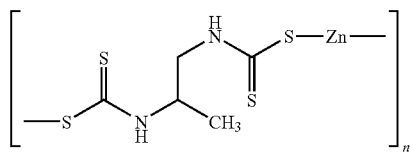

(7-5) thiram (known from U.S. Pat. No. 1,972,961) of the formula

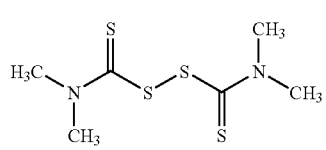

(7-6) zineb (known from DE-A 10 81 446) of the formula

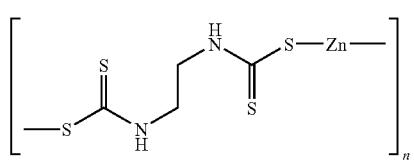

(7-7) ziram (known from U.S. Pat. No. 2,588,428) of the formula

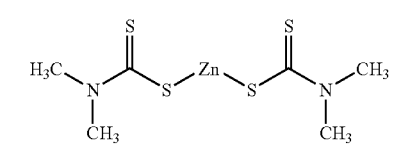

Group (8) Acylalanines
(8-1) benalaxyl (known from DE-A 29 03 612) of the formula

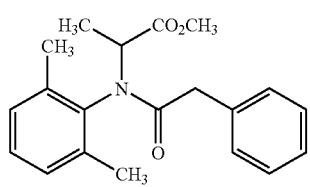

(8-2) furalaxyl (known from DE-A 25 13 732) of the formula

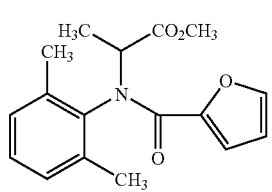 [SMILES: COC(=O)C(C)N(C(=O)c1ccco1)c1c(C)cccc1C]

(8-3) benalaxyl-M of the formula

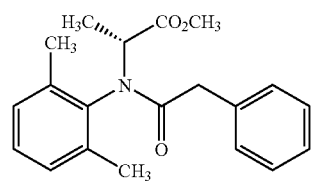 [SMILES: COC(=O)[C@@H](C)N(C(=O)Cc1ccccc1)c1c(C)cccc1C]

Group (9): Anilinopyrimidines
(9-1) cyprodinil (known from EP-A 0 310 550) of the formula

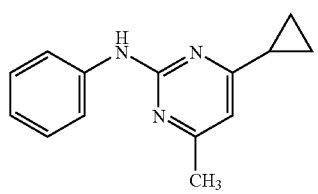 [SMILES: Cc1cc(C2CC2)nc(Nc2ccccc2)n1]

(9-2) pyrimethanil (known from DD 151 404) of the formula

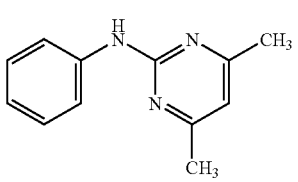

Group (10): Benzimidazoles
(10-1) 6-chloro-5-[(3,5-dimethylisoxazol-4-yl)sulfonyl]-2,2-difluoro-5H-[1,3]dioxolo[4,5-f]-benzimidazole (known from WO 97/06171) of the formula

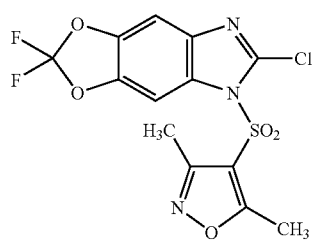 [SMILES: Cc1noc(C)c1S(=O)(=O)n1c(Cl)nc2cc3c(cc21)OC(F)(F)O3]

(10-2) benomyl (known from U.S. Pat. No. 3,631,176) of the formula

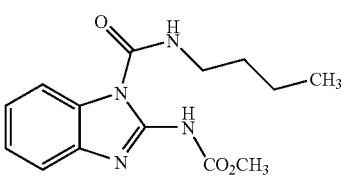 [SMILES: CCCCNC(=O)n1c(NC(=O)OC)nc2ccccc21]

(10-3) carbendazim (known from U.S. Pat. No. 3,010,968) of the formula

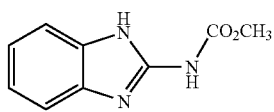 [SMILES: COC(=O)Nc1nc2ccccc2[nH]1]

(10-4) chlorfenazole of the formula

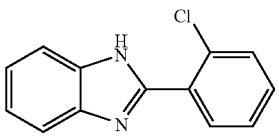 [SMILES: Clc1ccccc1-c1nc2ccccc2[nH]1]

(10-5) fuberidazole (known from DE-A 12 09 799) of the formula

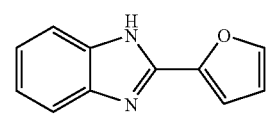 [SMILES: c1coc(-c2nc3ccccc3[nH]2)c1]

(10-6) thiabendazole (known from U.S. Pat. No. 3,206,468) of the formula

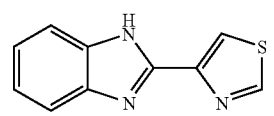

Group (11): Carbamates
(11-1) propamocarb (known from U.S. Pat. No. 3,513,241) of the formula

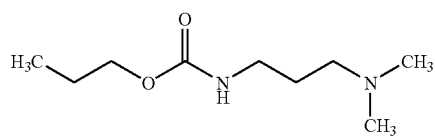

(11-2) propamocarb hydrochloride (known from U.S. Pat. No. 3,513,241) of the formula

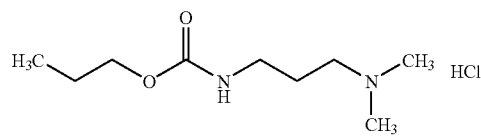

(11-3) propamocarb-fosetyl of the formula

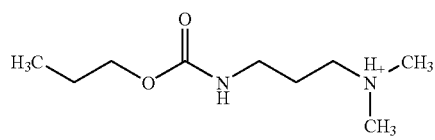

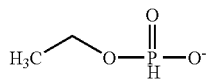

Group (12): Dicarboximides
(12-1) captafol (known from U.S. Pat. No. 3,178,447) of the formula

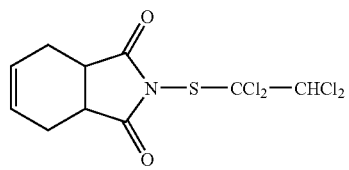

(12-2) folpet (known from U.S. Pat. No. 2,553,770) of the formula

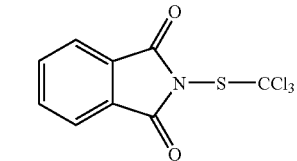

(12-3) iprodione (known from DE-A 21 49 923) of the formula

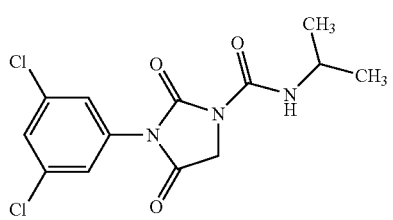 [SMILES: CC(C)NC(=O)N1CC(=O)N(c2cc(Cl)cc(Cl)c2)C1=O]

(12-4) procymidone (known from DE-A 20 12 656) of the formula

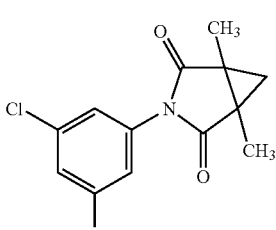

(12-5) vinclozolin (known from DE-A 22 07 576) of the formula

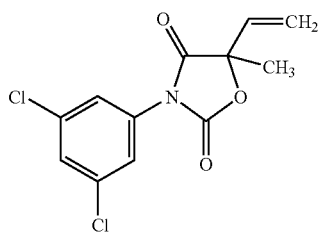 [SMILES: C=CC1(C)OC(=O)N(c2cc(Cl)cc(Cl)c2)C1=O]

Group (13): Guanidines
(13-1) dodine (known from GB 11 03 989) of the formula

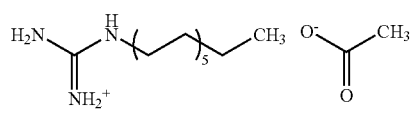

(13-2) guazatine (known from GB 11 14 155)
(13-3) iminoctadine triacetate (known from EP-A 0 155 509) of the formula

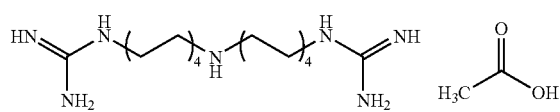

Group (14): Imidazoles
(14-1) cyazofamid (known from EP-A 0 298 196) of the formula

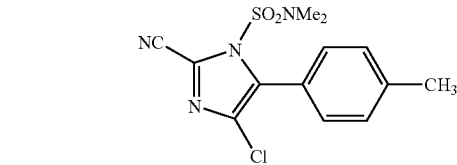

(14-2) prochloraz (known from DE-A 24 29 523) of the formula

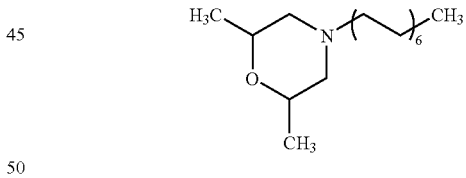

(14-3) triazoxide (known from DE-A 28 02 488) of the formula (14-4) pefurazoate (known from EP-A 0 248 086) of the formula

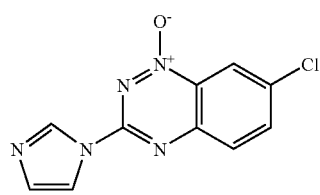 [SMILES: [O-][n+]1nc(-n2ccnc2)nc2ccc(Cl)cc21]

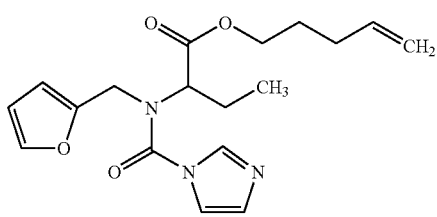 [SMILES: C=CCCCOC(=O)C(CC)N(Cc1ccco1)C(=O)n1ccnc1]

Group (15): Morpholines
(15-1) aldimorph (known from DD 140 041) of the formula

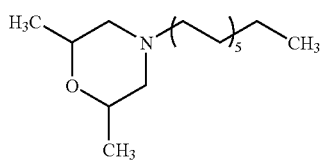

(15-2) tridemorph (known from GB 988 630) of the formula

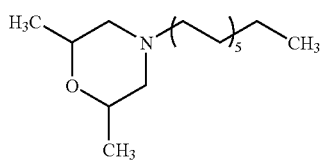

(15-3) dodemorph (known from DE-A 25 432 79) of the formula

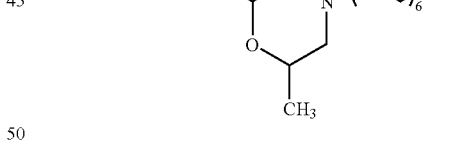

(15-4) fenpropimorph (known from DE-A 26 56 747) of the formula

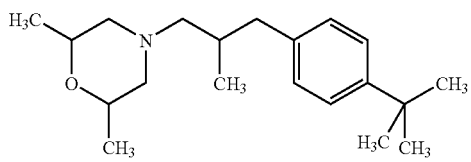 [SMILES: CC(Cc1ccc(C(C)(C)C)cc1)CN1CC(C)OC(C)C1]

Group (16): Pyrroles (16-1) fenpiclonil (known from EP-A 0 236 272) of the formula

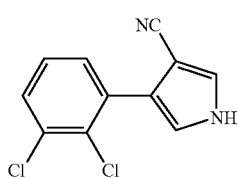

(16-2) pyrrolnitrine (known from JP 65-25876) of the formula

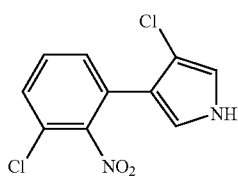 [SMILES: O=[N+]([O-])c1c(Cl)cccc1-c1c[nH]cc1Cl]

Group (17): Phosphonates (17-1) phosphonic acid (known as Chemikalie) of the formula

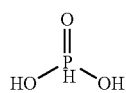

Group (18): Phenylethanamide (Known from WO 96/23793, in Each Case as E or Z Isomer, Preferably as E Isomer)

(18-1) the compound 2-(2,3-dihydro-1H-inden-5-yl)-N-[2-(3,4-dimethoxyphenyl)ethyl]-2-(methoxyimino)acetamide of the formula

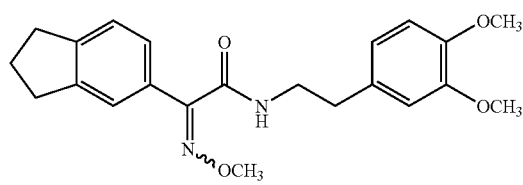 [SMILES: CON=C(C(=O)NCCc1ccc(OC)c(OC)c1)c1ccc2c(c1)CCC2]

(18-2) the compound N-[2-(3,4-dimethoxyphenyl)ethyl]-2-(methoxyimino)-2-(5,6,7,8-tetrahydro-naphthalen-2-yl)acetamide of the formula

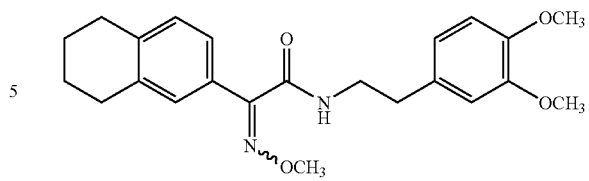

(18-3) the compound 2-(4-chlorophenyl)-N-[2-(3,4-dimethoxyphenyl)ethyl]-2-(methoxyimino)acetamide of the formula

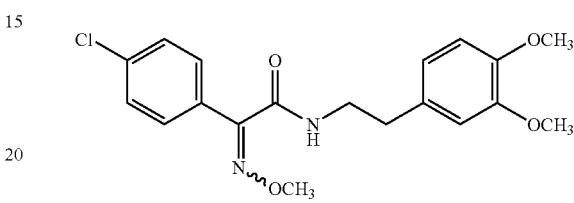

(18-4) the compound 2-(4-bromophenyl)-N-[2-(3,4-dimethoxyphenyl)ethyl]-2-(methoxyimino)acetamide of the formula

(18-5) the compound 2-(4-methylphenyl)-N-[2-(3,4-dimethoxyphenyl)ethyl]-2-(methoxyimino)-acetamide of the formula

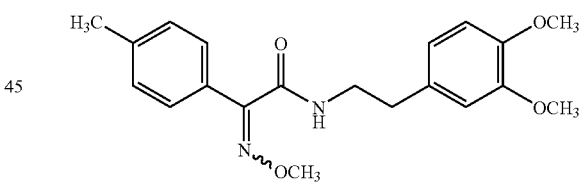

(18-6) the compound 2-(4-ethylphenyl)-N-[2-(3,4-dimethoxyphenyl)ethyl]-2-(methoxyimino)acetamide of the formula

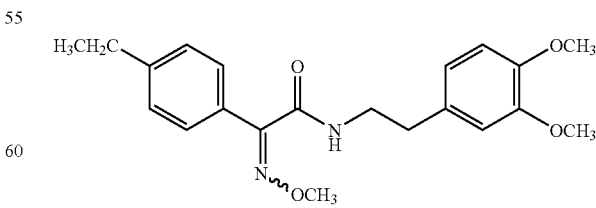

Group (19): Fungicides (19-1) acibenzolar-S-methyl (known from EP-A 0 313 512) of the formula

(19-2) edifenphos (known from DE-A 14 93 736) of the formula

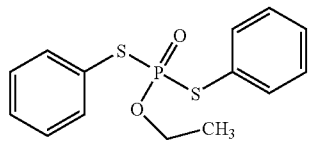 [SMILES: CCOP(=O)(Sc1ccccc1)Sc1ccccc1]

(19-3) famoxadone (known from EP-A 0 393 911) of the formula

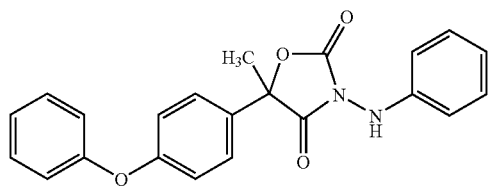 [SMILES: CC1(c2ccc(Oc3ccccc3)cc2)OC(=O)N(Nc2ccccc2)C1=O]

(19-4) oxadixyl (known from DE-A 30 30 026) of the formula (19-5) spiroxamine (known from DE-A 37 35 555) of the formula

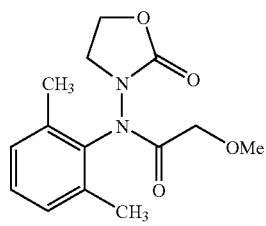

(19-6) dithianon (known from JP-A 44-29464) of the formula

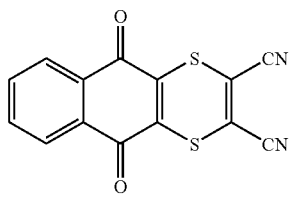 [SMILES: N#Cc1sc2c(=O)c3ccccc3c(=O)c=2sc1C#N]

(19-7) metrafenone (known from EP-A 0 897 904) of the formula

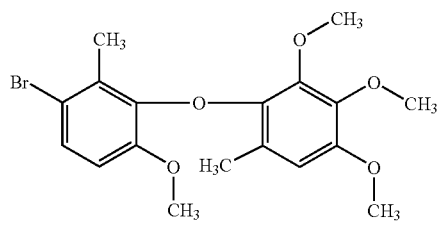

(19-8) fenamidone (known from EP-A 0 629 616) of the formula

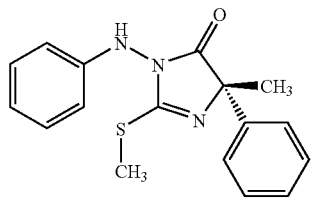 [SMILES: CSC1=N[C@@](C)(c2ccccc2)C(=O)N1Nc1ccccc1]

(19-9) 2,3-dibutyl-6-chlorothieno[2,3-d]pyrimidin-4(3H)one (known from WO 99/14202) of the formula

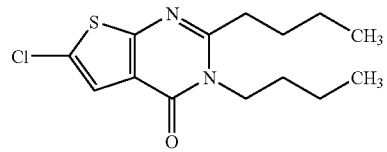 [SMILES: CCCCc1nc2sc(Cl)cc2c(=O)n1CCCC]

(19-10) probenazole (known from U.S. Pat. No. 3,629,428) of the formula

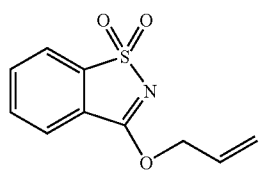

(19-11) isoprothiolane (known from U.S. Pat. No. 3,856,814) of the formula

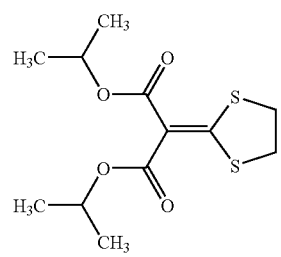

(19-12) kasugamycin (known from GB 1 094 567) of the formula

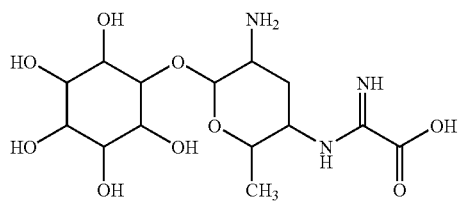 [SMILES: CC1OC(OC2C(O)C(O)C(O)C(O)C2O)C(N)CC1NC(=N)C(=O)O]

(19-13) phthalide (known from JP-A 57-55844) of the formula (19-14) N-({4-[(cyclopropylamino)carbonyl]phenyl}sulfonyl)-2-methoxybenzamide of the formula (19-15) 2-(4-chlorophenyl)-N-{2-[3-methoxy-4-(prop-2-yn-1-yloxy)phenyl]ethyl}-2-(prop-2-yn-1-yloxy)acetamide (known from WO 01/87822) of the formula (19-16) quinoxyfen (known from EP-A 0 326 330) of the formula (19-17) proquinazid (known from WO 94/26722) of the formula Group (20): (Thio)urea Derivatives (20-1) pencycuron (known from DE-A 27 32 257) of the formula (20-2) thiophanate-ethyl (known from DE-A 18 06 123) of the formula Group (21): Amides (21-1) fenoxanil (known from EP-A 0 262 393) of the formula

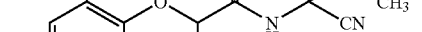

(21-2) diclocymet (known from JP-A 7-206608) of the formula

Group (22): Triazolopyrimidines (22-1) 5-chloro-N-[(1S)-2,2,2-trifluoro-1-methylethyl]-6-(2,4,6-trifluorophenyl)[1,2,4]triazolo[1,5-a]pyrimidine-7-amine (known from U.S. Pat. No. 5,986,135) of the formula

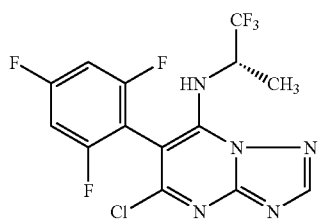 [SMILES: C[C@H](Nc1c(-c2c(F)cc(F)cc2F)c(Cl)nc2ncnn12)C(F)(F)F]

(22-2) 5-chloro-N-[(1R)-1,2-dimethylpropyl]-6-(2,4,6-trifluorophenyl)[1,2,4]triazolo[1,5-a]pyrimidine-7-amine (known from WO 02/38565) of the formula

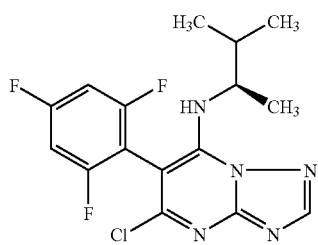 [SMILES: CC(C)[C@@H](C)Nc1c(-c2c(F)cc(F)cc2F)c(Cl)nc2ncnn12]

(22-3) 5-chloro-6-(2-chloro-6-fluorophenyl)-7-(4-methylpiperidin-1-yl)[1,2,4]triazolo[1,5-a]pyrimidine (known from U.S. Pat. No. 5,593,996) of the formula

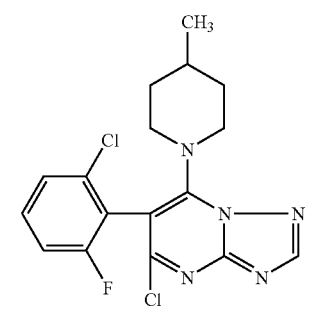 [SMILES: CC1CCN(c2c(-c3c(F)cccc3Cl)c(Cl)nc3ncnn23)CC1]

(22-4) 5-chloro-6-(2,4,6-trifluorophenyl)-7-(4-methylpiperidin-1-yl)[1,2,4]triazolo[1,5-a]pyrimidine (known from DE-A 101 24 208) of the formula

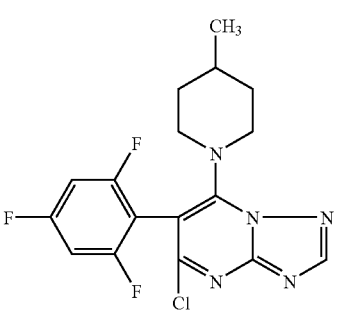 [SMILES: CC1CCN(c2c(-c3c(F)cc(F)cc3F)c(Cl)nc3ncnn23)CC1]

(22-5) 5-chloro-6-(2,4,6-trifluorophenyl)-N-[(1S)-1,2,2-trimethylpropyl][1,2,4]triazolo[1,5-a]pyrimidine-7-amine (known from U.S. Pat. No. 5,593,996) of the formula

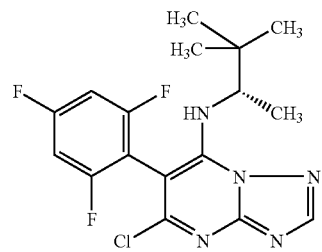 [SMILES: C[C@H](Nc1c(-c2c(F)cc(F)cc2F)c(Cl)nc2ncnn12)C(C)(C)C]

Group (23): Iodochromones (23-1) 2-butoxy-6-iodo-3-propylbenzopyran-4-one (known from WO 03/014103) of the formula

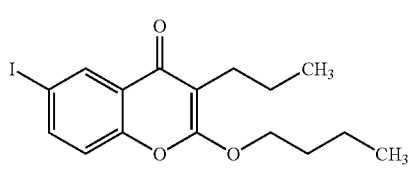 [SMILES: CCCCOc1oc2ccc(I)cc2c(=O)c1CCC]

(23-2) 2-ethoxy-6-iodo-3-propylbenzopyran-4-one (known from WO 03/014103) of the formula

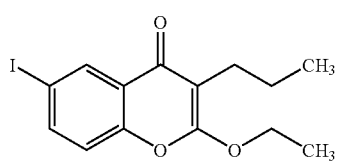 [SMILES: CCCc1c(OCC)oc2ccc(I)cc2c1=O]

(23-3) 6-iodo-2-propoxy-3-propylbenzopyran-4-one (known from WO 03/014103) of the formula

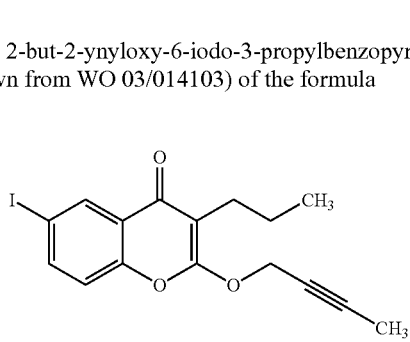

(23-4) 2-but-2-ynyloxy-6-iodo-3-propylbenzopyran-4-one (known from WO 03/014103) of the formula (23-5) 6-iodo-2-(1-methylbutoxy)-3-propylbenzopyran-4-one (known from WO 03/014103) of the formula

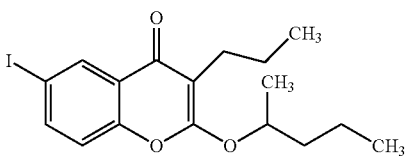 [SMILES: CCCc1c(OC(C)CCC)oc2ccc(I)cc2c1=O]

(23-6) 2-but-3-enyloxy-6-iodobenzopyran-4-one (known from WO 03/014103) of the formula

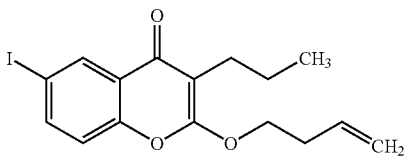 [SMILES: C=CCCOc1oc2ccc(I)cc2c(=O)c1CCC]

(23-7) 3-butyl-6-iodo-2-isopropoxybenzopyran-4-one (known from WO 03/014103) of the formula

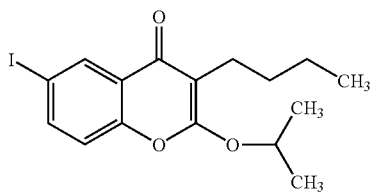 [SMILES: CCCCc1c(OC(C)C)oc2ccc(I)cc2c1=O]

Surprisingly, the fungicidal activity of the active compound combinations according to the invention is substantially higher than the sum of the activities of the individual active compounds. Thus, an unforeseeable true synergistic effect is present, and not just an addition of activities. The formula (I) provides a general definition of the compounds of group (1).

Preference is given to carboxamides of the formula (I) in which
R represents hydrogen or methyl,
G represents hydrogen or methyl,
$R^1$ represents hydrogen, fluorine, chlorine, methyl, ethyl, n-propyl, isopropyl, monofluoromethyl, difluoromethyl, trifluoromethyl, monochloromethyl, dichloromethyl or trichloromethyl,
A represents one of the radicals A1 or A2 below:

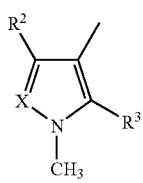

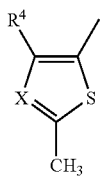

X represents CH or N,
$R^2$ represents methyl, difluoromethyl or trifluoromethyl,
$R^3$ represents hydrogen or fluorine,
$R^4$ represents difluoromethyl or trifluoromethyl.

The formula (I) comprises in particular the following preferred mixing partners of group (1):
(1-1) N-[2-(1,3-dimethylbutyl)-3-thienyl]-1-methyl-3-(trifluoromethyl)-1H-pyrazole-4-carboxamide
(1-2) 1-methyl-3-(trifluoromethyl)-N-[2-(1,3,3-trimethylbutyl)-3-thienyl]-1H-pyrazole-4-carboxamide
(1-3) 1-methyl-N-[2-(3-methylbutyl)-3-thienyl]-3-(trifluoromethyl)-1H-pyrazole-4-carboxamide
(1-4) N-[2-(3,3-dimethylbutyl)-3-thienyl]-1-methyl-3-(trifluoromethyl)-1H-pyrazole-4-carboxamide
(1-5) 3-(difluoromethyl)-N-[2-(1,3-dimethylbutyl)-3-thienyl]-1-methyl-1H-pyrazole-4-carboxamide
(1-6) 3-(difluoromethyl)-1-methyl-N-[2-(1,3,3-trimethylbutyl)-3-thienyl]-1H-pyrazole-4-carboxamide
(1-7) 3-(difluoromethyl)-1-methyl-N-[2-(3-methylbutyl)-3-thienyl]-1H-pyrazole-4-carboxamide
(1-8) 3-(difluoromethyl)-N-[2-(3,3-dimethylbutyl)-3-thienyl]-1-methyl-1H-pyrazole-4-carboxamide
(1-9) N-[2-(1,3-dimethylbutyl)-3-thienyl]-5-fluoro-1,3-dimethyl-1H-pyrazole-4-carboxamide
(1-10) 5-fluoro-1,3-dimethyl-N-[2-(1,3,3-trimethylbutyl)-3-thienyl]-1H-pyrazole-4-carboxamide
(1-11) 5-fluoro-1,3-dimethyl-N-[2-(3-methylbutyl)-3-thienyl]-1H-pyrazole-4-carboxamide
(1-12) N-[2-(3,3-dimethylbutyl)-3-thienyl]-5-fluoro-1,3-dimethyl-1H-pyrazole-4-carboxamide
(1-13) N-[2-(1,3-dimethylbutyl)-3-thienyl]-1-methyl-4-(trifluoromethyl)-1H-pyrrole-3-carboxamide
(1-14) 1-methyl-N-[2-(3-methylbutyl)-3-thienyl]-3-(trifluoromethyl)-1H-pyrrole-4-carboxamide
(1-15) N-[2-(3,3-dimethylbutyl)-3-thienyl]-1-methyl-3-(trifluoromethyl)-1H-pyrrole-4-carboxamide
(1-16) N-[2-(3,3-dimethylbutyl)-3-thienyl]-1-methyl-3-(trifluoromethyl)-1H-pyrrole-4-carboxamide
(1-17) 4-(difluoromethyl)-N-[2-(1,3-dimethylbutyl)-3-thienyl]-1-methyl-1H-pyrrole-3-carboxamide
(1-18) 4-(difluoromethyl)-1-methyl-N-[2-(1,3,3-trimethylbutyl)-3-thienyl]-1H-pyrrole-3-carboxamide
(1-19) 4-(difluoromethyl)-1-methyl-N-[2-(3-methylbutyl)-3-thienyl]-1H-pyrrole-3-carboxamide
(1-20) 4-(difluoromethyl)-N-[2-(3,3-dimethylbutyl)-3-thienyl]-1-methyl-1H-pyrrole-3-carboxamide
(1-21) N-[2-(1,3-dimethylbutyl)-3-thienyl]-2-fluoro-1,4-dimethyl-1H-pyrrole-3-carboxamide
(1-22) 5-fluoro-1,4-dimethyl-N-[2-(1,3,3-trimethylbutyl)-3-thienyl]-1H-pyrrole-3-carboxamide
(1-23) 5-fluoro-1,4-dimethyl-N-[2-(3-methylbutyl)-3-thienyl]-1H-pyrrole-3-carboxamide
(1-24) N-[2-(3,3-dimethylbutyl)-3-thienyl]-5-fluoro-1,4-dimethyl-1H-pyrrole-3-carboxamide
(1-25) N-[2-(1,3-dimethylbutyl)-3-thienyl]-2-methyl-4-(trifluoromethyl)-1,3-thiazole-5-carboxamide
(1-26) 2-methyl-4-(trifluoromethyl)-N-[2-(1,3,3-trimethylbutyl)-3-thienyl]-1,3-thiazole-5-carboxamide
(1-27) 2-methyl-N-[2-(3-methylbutyl)-3-thienyl]-4-(trifluoromethyl)-1,3-thiazole-5-carboxamide
(1-28) N-[2-(3,3-dimethylbutyl)-3-thienyl]-2-methyl-4-(trifluoromethyl)-1,3-thiazole-5-carboxamide
(1-29) 4-(difluoromethyl)-N-[2-(1,3-dimethylbutyl)-3-thienyl]-2-methyl-1,3-thiazole-5-carboxamide
(1-30) 4-(difluoromethyl)-2-methyl-N-[2-(1,3,3-trimethylbutyl)-3-thienyl]-1,3-thiazole-5-carboxamide (1-31) 4-(difluoromethyl)-2-methyl-N-[2-(3-methylbutyl)-3-thienyl]-1,3-thiazole-5-carboxamide (1-32) 4-(difluoromethyl)-N-[2-(3,3-dimethylbutyl)-3-thienyl]-2-methyl-1,3-thiazole-5-carboxamide Emphasis is given to active compound combinations according to the invention comprising in addition to the carboxamide (1-1) N-[2-(1,3-dimethylbutyl)-3-thienyl]-1-methyl-3-(trifluoromethyl)-1H-pyrazole-4-carboxamide (group 1) one or more, preferably one, mixing partner from groups (2) to (23).

Emphasis is given to active compound combinations according to the invention comprising in addition to the carboxamide (1-9) N-[2-(1,3-dimethylbutyl)-3-thienyl]-5-fluoro-1,3-dimethyl-1H-pyrazole-4-carboxamide (group 1) one or more, preferably one, mixing partner from groups (2) to (23).

Emphasis is given to active compound combinations according to the invention comprising in addition to the carboxamide (1-13) N-[2-(1,3-dimethylbutyl)-3-thienyl]-1-methyl-4-(trifluoromethyl)-1H-pyrrole-3-carboxamide (group 1) one or more, preferably one, mixing partner from groups (2) to (23).

Emphasis is given to active compound combinations according to the invention comprising in addition to the carboxamide (1-25) N-[2-(1,3-dimethylbutyl)-3-thienyl]-2-methyl-4-(trifluoromethyl)-1,3-thiazole-5-carboxamide (group 1) one or more, preferably one, mixing partner from groups (2) to (23).

The compound (6-6) carpropamid has three asymmetrically substituted carbon atoms. Accordingly, the compound (6-7) can be present as a mixture of various isomers or else in the form of a single component. Particular preference is given to the compounds (1S,3R)-2,2-dichloro-N-[(1R)-1-(4-chlorophenyl)ethyl]-1-ethyl-3-methylcyclopropanecarboxamide of the formula

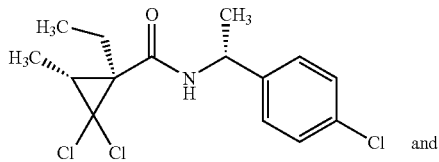 [SMILES: CC[C@@]1(C(=O)N[C@H](C)c2ccc(Cl)cc2)[C@@H](C)C1(Cl)Cl ; "and"]

(1R,3S)-2,2-dichloro-N-[(1R)-1-(4-chlorophenyl)ethyl]-1-ethyl-3-methylcyclopropanecarboxamide of the formula

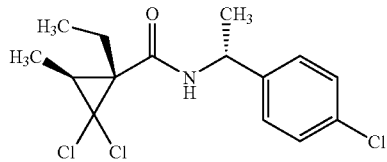

Preferred mixing partners are the following active compounds of groups (2) to (23):

(2-1) fluoxastrobin, (2-2) (2E)-2-(2-{[6-(3-chloro-2-methylphenoxy)-5-fluoro-4-pyrimidinyl]oxy}-phenyl)-2-(methoxyimino)-N-methylethanamide, (2-3) trifloxystrobin, (2-4) (2E)-2-(methoxyimino)-N-methyl-2-(2-{[({(1E)-1-[3-(trifluoromethyl)phenyl]ethylidene}amino)oxy]methyl}phenyl)ethanamide, (2-5) (2E)-2-(methoxyimino)-N-methyl-2-{2-[(E)-({1-[3-(trifluoromethyl)phenyl]ethoxy}imino)methyl]phenyl}ethanamide, (2-7) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (2-8) dimoxystrobin, (2-9) picoxystrobin, (2-10) pyraclostrobin, (3-3) propiconazole, (3-4) difenoconazole, (3-6) cyproconazole, (3-7) hexaconazole, (3-8) penconazole, (3-9) myclobutanil, (3-10) tetraconazole, (3-13) flusilazole, (3-15) prothioconazole, (3-16) fenbuconazole, (3-17) tebuconazole, (3-21) bitertanol, (3-22) triadimenol, (3-23) triadimefon, (3-12) epoxiconazole, (3-19) metconazole, (3-24) fluquinconazole, (4-1) dichlofluanid, (4-2) tolylfluanid, (5-1) iprovalicarb, (5-2) benthiavalicarb, (6-2) boscalid, (6-4) ethaboxam, (6-5) fenhexamid, (6-6) carpropamid, (6-7) 2-chloro-4-[(2-fluoro-2-methylpropanoyl)amino]-N,N-dimethylbenzamide, (6-8) picobenzamid, (6-9) zoxamide, (6-10) 3,4-dichloro-N-(2-cyanophenyl)isothiazole-5-carboxamide, (7-1) mancozeb, (7-2) maneb, (7-4) propineb, (7-5) thiram, (7-6) zineb, (8-1) benalaxyl, (8-2) furalaxyl, (8-3) benalaxyl-M, (9-1) cyprodinil, (9-2) pyrimethanil, (10-1) 6-chloro-5-[(3,5-dimethylisoxazol-4-yl)sulfonyl]-2,2-difluoro-5H-[1,3]dioxolo[4,5-f]benzimidazole, (10-3) carbendazim, (11-1) propamocarb, (11-2) propamocarb hydrochloride, (11-3) propamocarb-fosetyl, (12-2) folpet, (12-3) iprodione, (12-4) procymidone, (13-1) dodine, (13-2) guazatine, (13-3) iminoctadine triacetate, (14-1) cyazofamid, (14-2) prochloraz, (14-3) triazoxide, (15-4) fenpropimorph, (17-1) phosphonic acid, (19-1) acibenzolar-S-methyl, (19-3) famoxadone, (19-4) oxadixyl, (19-5) spiroxamine, (19-8) fenamidone, (19-15) 2-(4-chlorophenyl)-N-{2-[3-methoxy-4-(prop-2-yn-1-yloxy)phenyl]ethyl}-2-(prop-2-yn-1-yloxy)acetamide, (19-16) quinoxyfen, (19-17) proquinazid, (20-1) pencycuron, (22-1) 5-chloro-N-[(1S)-2,2,2-trifluoro-1-methylethyl]-6-(2,4,6-trifluorophenyl)[1,2,4]triazolo[1,5-a]pyrimidine-7-amine, (22-2) 5-chloro-N-[(1R)-1,2-dimethylpropyl]-6-(2,4,6-trifluorophenyl)[1,2,4]triazolo[1,5-a]pyrimidine-7-amine, (22-4) 5-chloro-6-(2,4,6-trifluorophenyl)-7-(4-methylpiperidin-1-yl)[1,2,4]triazolo[1,5-a]pyrimidine, (22-5) 5-chloro-6-(2,4,6-trifluorophenyl)-N-[(1S)-1,2,2-trimethylpropyl][1,2,4]triazolo[1,5-a]pyrimidine-7-amine, (23-1) 2-butoxy-6-iodo-3-propylbenzopyran-4-one, (23-2) 2-ethoxy-6-iodo-3-propylbenzopyran-4-one, (23-3) 6-iodo-2-propoxy-3-propylbenzopyran-4-one.

Particularly preferred mixing partners are the following active compounds of groups (2) to (23):

(2-1) fluoxastrobin, (2-2) (2E)-2-(2-{[6-(3-chloro-2-methylphenoxy)-5-fluoro-4-pyrimidinyl]oxy}-phenyl)-2-(methoxyimino)-N-methylethanamide, (2-3) trifloxystrobin, (3-15) prothioconazole, (3-17) tebuconazole, (3-21) bitertanol, (3-22) triadimenol, (3-24) fluquinconazole, (4-1) dichlofluanid, (4-2) tolylfluanid, (5-1) iprovalicarb, (6-5) fenhexamid, (6-6) carpropamid, (6-8) picobenzamid, (7-4) propineb, (8-3) benalaxyl-M, (9-2) pyrimethanil, (10-3) carbendazim, (11-3) propamocarb-fosetyl, (12-3) iprodione, (14-2) prochloraz, (14-3) triazoxide, (19-5) spiroxamine, (19-15) 2-(4-chlorophenyl)-N-{2-[3-methoxy-4-(prop-2-yn-1-yloxy)phenyl]ethyl}-2-(prop-2-yn-1-yloxy)acetamide, (22-4) 5-chloro-6-(2,4,6-trifluorophenyl)-7-(4-methylpiperidin-1-yl)[1,2,4]triazolo[1,5-a]pyrimidine, (22-5) 5-chloro-6-(2,4,6-trifluorophenyl)-N-[(1S)-1,2,2-trimethylpropyl][1,2,4]triazolo[1,5-a]pyrimidine-7-amine.

Hereinbelow, preferred active compound combinations consisting of two groups of active compounds and comprising in each case at least one carboxamide of the formula (I) (group 1) and at least one active compound from the stated group (2) to (23) are described. These combinations are the active compound combinations A to R.

Preference is given to active compound combinations A to R in which the carboxamide of the formula (I) (group 1) is selected from the list below:
- (1-1) N-[2-(1,3-dimethylbutyl)-3-thienyl]-1-methyl-3-(trifluoromethyl)-1H-pyrazole-4-carboxamide
- (1-3) 1-methyl-N-[2-(3-methylbutyl)-3-thienyl]-3-(trifluoromethyl)-1H-pyrazole-4-carboxamide
- (1-5) 3-(difluoromethyl)-N-[2-(1,3-dimethylbutyl)-3-thienyl]-1-methyl-1H-pyrazole-4-carboxamide
- (1-7) 3-(difluoromethyl)-1-methyl-N-[2-(3-methylbutyl)-3-thienyl]-1H-pyrazole-4-carboxamide
- (1-9) N-[2-(1,3-dimethylbutyl)-3-thienyl]-5-fluoro-1,3-dimethyl-1H-pyrazole-4-carboxamide
- (1-11) 5-fluoro-1,3-dimethyl-N-[2-(3-methylbutyl)-3-thienyl]-1H-pyrazole-4-carboxamide
- (1-13) N-[2-(1,3-dimethylbutyl)-3-thienyl]-1-methyl-4-(trifluoromethyl)-1H-pyrrole-3-carboxamide
- (1-15) N-[2-(3,3-dimethylbutyl)-3-thienyl]-1-methyl-3-(trifluoromethyl)-1H-pyrrole-4-carboxamide
- (1-17) 4-(difluoromethyl)-N-[2-(1,3-dimethylbutyl)-3-thienyl]-1-methyl-1H-pyrrole-3-carboxamide
- (1-19) 4-(difluoromethyl)-1-methyl-N-[2-(3-methylbutyl)-3-thienyl]-1H-pyrrole-3-carboxamide
- (1-21) N-[2-(1,3-dimethylbutyl)-3-thienyl]-2-fluoro-1,4-dimethyl-1H-pyrrole-3-carboxamide
- (1-23) 5-fluoro-1,4-dimethyl-N-[2-(3-methylbutyl)-3-thienyl]-1H-pyrrole-3-carboxamide
- (1-25) N-[2-(1,3-dimethylbutyl)-3-thienyl]-2-methyl-4-(trifluoromethyl)-1,3-thiazole-5-carboxamide
- (1-27) 2-methyl-N-[2-(3-methylbutyl)-3-thienyl]-4-(trifluoromethyl)-1,3-thiazole-5-carboxamide
- (1-29) 4-(difluoromethyl)-N-[2-(1,3-dimethylbutyl)-3-thienyl]-2-methyl-1,3-thiazole-5-carboxamide
- (1-31) 4-(difluoromethyl)-2-methyl-N-[2-(3-methylbutyl)-3-thienyl]-1,3-thiazole-5-carboxamide Particular preference is given to active compound combinations A to R in which the carboxamide of the formula (I) (group 1) is selected from the list below:
- (1-1) N-[2-(1,3-dimethylbutyl)-3-thienyl]-1-methyl-3-(trifluoromethyl)-1H-pyrazole-4-carboxamide
- (1-5) 3-(difluoromethyl)-N-[2-(1,3-dimethylbutyl)-3-thienyl]-1-methyl-1H-pyrazole-4-carboxamide
- (1-9) N-[2-(1,3-dimethylbutyl)-3-thienyl]-5-fluoro-1,3-dimethyl-1H-pyrazole-4-carboxamide
- (1-13) N-[2-(1,3-dimethylbutyl)-3-thienyl]-1-methyl-4-(trifluoromethyl)-1H-pyrrole-3-carboxamide
- (1-17) 4-(difluoromethyl)-N-[2-(1,3-dimethylbutyl)-3-thienyl]-1-methyl-1H-pyrrole-3-carboxamide
- (1-21) N-[2-(1,3-dimethylbutyl)-3-thienyl]-2-fluoro-1,4-dimethyl-1H-pyrrole-3-carboxamide
- (1-25) N-[2-(1,3-dimethylbutyl)-3-thienyl]-2-methyl-4-(trifluoromethyl)-1,3-thiazole-5-carboxamide
- (1-29) 4-(difluoromethyl)-N-[2-(1,3-dimethylbutyl)-3-thienyl]-2-methyl-1,3-thiazole-5-carboxamide Preference is given to active compound combinations A in which the strobilurin (group 2) is selected from the list below: (2-1) fluoxastrobin, (2-2) (2E)-2-(2-{[6-(3-chloro-2-methylphenoxy)-5-fluoro-4-pyrimidinyl]oxy}phenyl)-2-(methoxyimino)-N-methylethanamide, (2-3) trifloxystrobin, (2-4) (2E)-2-(methoxyimino)-N-methyl-2-(2-{[({(1E)-1-[3-(trifluoromethyl)phenyl]ethylidene}amino)oxy]methyl}-phenyl)ethanamide, (2-5) (2E)-2-(methoxyimino)-N-methyl-2-{2-[(E)-({1-[3-(trifluoromethyl)phenyl]-ethoxy}imino)methyl]phenyl}ethanamide, (2-6) orysastrobin, (2-7) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (2-8) dimoxystrobin, (2-9) picoxystrobin, (2-10) pyraclostrobin.

Particular preference is given to active compound combinations A in which the strobilurin (group 2) is selected from the following list: (2-1) fluoxastrobin, (2-2) (2E)-2-(2-{[6-(3-chloro-2-methylphenoxy)-5-fluoro-4-pyrimidinyl]oxy}phenyl)-2-(methoxyimino)-N-methylethanamide, (2-3) trifloxystrobin, (2-8) dimoxystrobin, (2-9) picoxystrobin, (2-10) pyraclostrobin.

Emphasis is given to the active compound combinations A listed in table 1 below:

TABLE 1

Active compound combinations A

| No. | Carboxamide of the formula (I) | Strobilurin (group 2) |
|---|---|---|
| A-1 | (1-1) N-[2-(1,3-dimethylbutyl)-3-thienyl]-1-methyl-3-(trifluoromethyl)-1H-pyrazole-4-carboxamide | (2-1) fluoxastrobin |
| A-2 | (1-1) N-[2-(1,3-dimethylbutyl)-3-thienyl]-1-methyl-3-(trifluoromethyl)-1H-pyrazole-4-carboxamide | (2-2) (2E)-2-(2-{[6-(3-chloro-2-methylphenoxy)-5-fluoro-4-pyrimidinyl]oxy}phenyl)-2-(methoxyimino)-N-methylethanamide |
| A-3 | (1-1) N-[2-(1,3-dimethylbutyl)-3-thienyl]-1-methyl-3-(trifluoromethyl)-1H-pyrazole-4-carboxamide | (2-3) trifloxystrobin |
| A-4 | (1-1) N-[2-(1,3-dimethylbutyl)-3-thienyl]-1-methyl-3-(trifluoromethyl)-1H-pyrazole-4-carboxamide | (2-8) dimoxystrobin |
| A-5 | (1-1) N-[2-(1,3-dimethylbutyl)-3-thienyl]-1-methyl-3-(trifluoromethyl)-1H-pyrazole-4-carboxamide | (2-9) picoxystrobin |
| A-6 | (1-1) N-[2-(1,3-dimethylbutyl)-3-thienyl]-1-methyl-3-(trifluoromethyl)-1H-pyrazole-4-carboxamide | (2-10) pyraclostrobin |
| A-7 | (1-9) N-[2-(1,3-dimethylbutyl)-3-thienyl]-5-fluoro-1,3-dimethyl-1H-pyrazole-4-carboxamide | (2-1) fluoxastrobin |
| A-8 | (1-9) N-[2-(1,3-dimethylbutyl)-3-thienyl]-5-fluoro-1,3-dimethyl-1H-pyrazole-4-carboxamide | (2-2) (2E)-2-(2-{[6-(3-chloro-2-methylphenoxy)-5-fluoro-4-pyrimidinyl]oxy}phenyl)-2-(methoxyimino)-N-methylethanamide |
| A-9 | (1-9) N-[2-(1,3-dimethylbutyl)-3-thienyl]-5-fluoro-1,3-dimethyl-1H-pyrazole-4-carboxamide | (2-3) trifloxystrobin |
| A-10 | (1-9) N-[2-(1,3-dimethylbutyl)-3-thienyl]-5-fluoro-1,3-dimethyl-1H-pyrazole-4-carboxamide | (2-8) dimoxystrobin |
| A-11 | (1-9) N-[2-(1,3-dimethylbutyl)-3-thienyl]-5-fluoro-1,3-dimethyl-1H-pyrazole-4-carboxamide | (2-9) picoxystrobin |
| A-12 | (1-9) N-[2-(1,3-dimethylbutyl)-3-thienyl]-5-fluoro-1,3-dimethyl-1H-pyrazole-4-carboxamide | (2-10) pyraclostrobin |

TABLE 1-continued

Active compound combinations A

| No. | Carboxamide of the formula (I) | Strobilurin (group 2) |
|---|---|---|
| A-13 | (1-13) N-[2-(1,3-dimethylbutyl)-3-thienyl]-1-methyl-4-(trifluoromethyl)-1H-pyrrole-3-carboxamide | (2-1) fluoxastrobin |
| A-14 | (1-13) N-[2-(1,3-dimethylbutyl)-3-thienyl]-1-methyl-4-(trifluoromethyl)-1H-pyrrole-3-carboxamide | (2-2) (2E)-2-(2-{[6-(3-chloro-2-methylphenoxy)-5-fluoro-4-pyrimidinyl]oxy}phenyl)-2-(methoxyimino)-N-methylethanamide |
| A-15 | (1-13) N-[2-(1,3-dimethylbutyl)-3-thienyl]-1-methyl-4-(trifluoromethyl)-1H-pyrrole-3-carboxamide | (2-3) trifloxystrobin |
| A-16 | (1-13) N-[2-(1,3-dimethylbutyl)-3-thienyl]-1-methyl-4-(trifluoromethyl)-1H-pyrrole-3-carboxamide | (2-8) dimoxystrobin |
| A-17 | (1-13) N-[2-(1,3-dimethylbutyl)-3-thienyl]-1-methyl-4-(trifluoromethyl)-1H-pyrrole-3-carboxamide | (2-9) picoxystrobin |
| A-18 | (1-13) N-[2-(1,3-dimethylbutyl)-3-thienyl]-1-methyl-4-(trifluoromethyl)-1H-pyrrole-3-carboxamide | (2-10) pyraclostrobin |
| A-19 | (1-25) N-[2-(1,3-dimethylbutyl)-3-thienyl]-2-methyl-4-(trifluoromethyl)-1,3-thiazole-5-carboxamide | (2-1) fluoxastrobin |
| A-20 | (1-25) N-[2-(1,3-dimethylbutyl)-3-thienyl]-2-methyl-4-(trifluoromethyl)-1,3-thiazole-5-carboxamide | (2-2) (2E)-2-(2-{[6-(3-chloro-2-methylphenoxy)-5-fluoro-4-pyrimidinyl]oxy}phenyl)-2-(methoxyimino)-N-methylethanamide |
| A-21 | (1-25) N-[2-(1,3-dimethylbutyl)-3-thienyl]-2-methyl-4-(trifluoromethyl)-1,3-thiazole-5-carboxamide | (2-3) trifloxystrobin |
| A-22 | (1-25) N-[2-(1,3-dimethylbutyl)-3-thienyl]-2-methyl-4-(trifluoromethyl)-1,3-thiazole-5-carboxamide | (2-8) dimoxystrobin |
| A-23 | (1-25) N-[2-(1,3-dimethylbutyl)-3-thienyl]-2-methyl-4-(trifluoromethyl)-1,3-thiazole-5-carboxamide | (2-9) picoxystrobin |
| A-24 | (1-25) N-[2-(1,3-dimethylbutyl)-3-thienyl]-2-methyl-4-(trifluoromethyl)-1,3-thiazole-5-carboxamide | (2-10) pyraclostrobin |

Preference is given to active compound combinations B in which the triazole (group 3) is selected from the following list: (3-1) azaconazole, (3-2) etaconazole, (3-3) propiconazole, (3-4) difenoconazole, (3-5) bromuconazole, (3-6) cyproconazole, (3-7) hexaconazole, (3-8) penconazole, (3-9) myclobutanil, (3-10) tetraconazole, (3-11) flutriafol, (3-12) epoxiconazole, (3-13) flusilazole, (3-14) simeconazole, (3-15) prothioconazole, (3-16) fenbuconazole, (3-17) tebuconazole, (3-18) ipconazole, (3-19) metconazole, (3-20) triticonazole, (3-21) bitertanol, (3-22) triadimenol, (3-23) triadimefon, (3-24) fluquinconazole, (3-25) quinconazole.

Particular preference is given to active compound combinations B in which the triazole (group 3) is selected from the following list: (3-3) propiconazole, (3-4) difenoconazole, (3-6) cyproconazole, (3-7) hexaconazole, (3-15) prothioconazole, (3-17) tebuconazole, (3-19) metconazole, (3-21) bitertanol, (3-22) triadimenol, (3-24) fluquinconazole.

Emphasis is given to the active compound combinations B listed in table 2 below:

TABLE 2

Active compound combinations B

| No. | Carboxamide of the formula (I) | Triazole (group 3) |
|---|---|---|
| B-1 | (1-1) N-[2-(1,3-dimethylbutyl)-3-thienyl]-1-methyl-3-(trifluoromethyl)-1H-pyrazole-4-carboxamide | (3-3) propiconazole |
| B-2 | (1-1) N-[2-(1,3-dimethylbutyl)-3-thienyl]-1-methyl-3-(trifluoromethyl)-1H-pyrazole-4-carboxamide | (3-4) difenoconazole |
| B-3 | (1-1) N-[2-(1,3-dimethylbutyl)-3-thienyl]-1-methyl-3-(trifluoromethyl)-1H-pyrazole-4-carboxamide | (3-6) cyproconazole |
| B-4 | (1-1) N-[2-(1,3-dimethylbutyl)-3-thienyl]-1-methyl-3-(trifluoromethyl)-1H-pyrazole-4-carboxamide | (3-7) hexaconazole |
| B-5 | (1-1) N-[2-(1,3-dimethylbutyl)-3-thienyl]-1-methyl-3-(trifluoromethyl)-1H-pyrazole-4-carboxamide | (3-15) prothioconazole |
| B-6 | (1-1) N-[2-(1,3-dimethylbutyl)-3-thienyl]-1-methyl-3-(trifluoromethyl)-1H-pyrazole-4-carboxamide | (3-17) tebuconazole |
| B-7 | (1-1) N-[2-(1,3-dimethylbutyl)-3-thienyl]-1-methyl-3-(trifluoromethyl)-1H-pyrazole-4-carboxamide | (3-19) metconazole |
| B-8 | (1-1) N-[2-(1,3-dimethylbutyl)-3-thienyl]-1-methyl-3-(trifluoromethyl)-1H-pyrazole-4-carboxamide | (3-21) bitertanol |
| B-9 | (1-1) N-[2-(1,3-dimethylbutyl)-3-thienyl]-1-methyl-3-(trifluoromethyl)-1H-pyrazole-4-carboxamide | (3-22) triadimenol |
| B-10 | (1-1) N-[2-(1,3-dimethylbutyl)-3-thienyl]-1-methyl-3-(trifluoromethyl)-1H-pyrazole-4-carboxamide | (3-24) fluquinconazole |
| B-11 | (1-9) N-[2-(1,3-dimethylbutyl)-3-thienyl]-5-fluoro-1,3-dimethyl-1H-pyrazole-4-carboxamide | (3-3) propiconazole |
| B-12 | (1-9) N-[2-(1,3-dimethylbutyl)-3-thienyl]-5-fluoro-1,3-dimethyl-1H-pyrazole-4-carboxamide | (3-4) difenoconazole |
| B-13 | (1-9) N-[2-(1,3-dimethylbutyl)-3-thienyl]-5-fluoro-1,3-dimethyl-1H-pyrazole-4-carboxamide | (3-6) cyproconazole |

TABLE 2-continued

Active compound combinations B

| No. | Carboxamide of the formula (I) | Triazole (group 3) |
| --- | --- | --- |
| B-14 | (1-9) N-[2-(1,3-dimethylbutyl)-3-thienyl]-5-fluoro-1,3-dimethyl-1H-pyrazole-4-carboxamide | (3-7) hexaconazole |
| B-15 | (1-9) N-[2-(1,3-dimethylbutyl)-3-thienyl]-5-fluoro-1,3-dimethyl-1H-pyrazole-4-carboxamide | (3-15) prothioconazole |
| B-16 | (1-9) N-[2-(1,3-dimethylbutyl)-3-thienyl]-5-fluoro-1,3-dimethyl-1H-pyrazole-4-carboxamide | (3-17) tebuconazole |
| B-17 | (1-9) N-[2-(1,3-dimethylbutyl)-3-thienyl]-5-fluoro-1,3-dimethyl-1H-pyrazole-4-carboxamide | (3-19) metconazole |
| B-18 | (1-9) N-[2-(1,3-dimethylbutyl)-3-thienyl]-5-fluoro-1,3-dimethyl-1H-pyrazole-4-carboxamide | (3-21) bitertanol |
| B-19 | (1-9) N-[2-(1,3-dimethylbutyl)-3-thienyl]-5-fluoro-1,3-dimethyl-1H-pyrazole-4-carboxamide | (3-22) triadimenol |
| B-20 | (1-9) N-[2-(1,3-dimethylbutyl)-3-thienyl]-5-fluoro-1,3-dimethyl-1H-pyrazole-4-carboxamide | (3-24) fluquinconazole |
| B-21 | (1-13) N-[2-(1,3-dimethylbutyl)-3-thienyl]-1-methyl-4-(trifluoromethyl)-1H-pyrrole-3-carboxamide | (3-3) propiconazole |
| B-22 | (1-13) N-[2-(1,3-dimethylbutyl)-3-thienyl]-1-methyl-4-(trifluoromethyl)-1H-pyrrole-3-carboxamide | (3-4) difenoconazole |
| B-23 | (1-13) N-[2-(1,3-dimethylbutyl)-3-thienyl]-1-methyl-4-(trifluoromethyl)-1H-pyrrole-3-carboxamide | (3-6) cyproconazole |
| B-24 | (1-13) N-[2-(1,3-dimethylbutyl)-3-thienyl]-1-methyl-4-(trifluoromethyl)-1H-pyrrole-3-carboxamide | (3-7) hexaconazole |
| B-25 | (1-13) N-[2-(1,3-dimethylbutyl)-3-thienyl]-1-methyl-4-(trifluoromethyl)-1H-pyrrole-3-carboxamide | (3-15) prothioconazole |
| B-26 | (1-13) N-[2-(1,3-dimethylbutyl)-3-thienyl]-1-methyl-4-(trifluoromethyl)-1H-pyrrole-3-carboxamide | (3-17) tebuconazole |
| B-27 | (1-13) N-[2-(1,3-dimethylbutyl)-3-thienyl]-1-methyl-4-(trifluoromethyl)-1H-pyrrole-3-carboxamide | (3-19) metconazole |
| B-28 | (1-13) N-[2-(1,3-dimethylbutyl)-3-thienyl]-1-methyl-4-(trifluoromethyl)-1H-pyrrole-3-carboxamide | (3-21) bitertanol |
| B-29 | (1-13) N-[2-(1,3-dimethylbutyl)-3-thienyl]-1-methyl-4-(trifluoromethyl)-1H-pyrrole-3-carboxamide | (3-22) triadimenol |
| B-30 | (1-13) N-[2-(1,3-dimethylbutyl)-3-thienyl]-1-methyl-4-(trifluoromethyl)-1H-pyrrole-3-carboxamide | (3-24) fluquinconazole |
| B-31 | (1-25) N-[2-(1,3-dimethylbutyl)-3-thienyl]-2-methyl-4-(trifluoromethyl)-1,3-thiazole-5-carboxamide | (3-3) propiconazole |
| B-32 | (1-25) N-[2-(1,3-dimethylbutyl)-3-thienyl]-2-methyl-4-(trifluoromethyl)-1,3-thiazole-5-carboxamide | (3-4) difenoconazole |
| B-33 | (1-25) N-[2-(1,3-dimethylbutyl)-3-thienyl]-2-methyl-4-(trifluoromethyl)-1,3-thiazole-5-carboxamide | (3-6) cyproconazole |
| B-34 | (1-25) N-[2-(1,3-dimethylbutyl)-3-thienyl]-2-methyl-4-(trifluoromethyl)-1,3-thiazole-5-carboxamide | (3-7) hexaconazole |
| B-35 | (1-25) N-[2-(1,3-dimethylbutyl)-3-thienyl]-2-methyl-4-(trifluoromethyl)-1,3-thiazole-5-carboxamide | (3-15) prothioconazole |
| B-36 | (1-25) N-[2-(1,3-dimethylbutyl)-3-thienyl]-2-methyl-4-(trifluoromethyl)-1,3-thiazole-5-carboxamide | (3-17) tebuconazole |
| B-37 | (1-25) N-[2-(1,3-dimethylbutyl)-3-thienyl]-2-methyl-4-(trifluoromethyl)-1,3-thiazole-5-carboxamide | (3-19) metconazole |
| B-38 | (1-25) N-[2-(1,3-dimethylbutyl)-3-thienyl]-2-methyl-4-(trifluoromethyl)-1,3-thiazole-5-carboxamide | (3-21) bitertanol |
| B-39 | (1-25) N-[2-(1,3-dimethylbutyl)-3-thienyl]-2-methyl-4-(trifluoromethyl)-1,3-thiazole-5-carboxamide | (3-22) triadimenol |
| B-40 | (1-25) N-[2-(1,3-dimethylbutyl)-3-thienyl]-2-methyl-4-(trifluoromethyl)-1,3-thiazole-5-carboxamide | (3-24) fluquinconazole |

Preference is given to active compound combinations C in which the sulfenamide (group 4) is selected from the following list: (4-1) dichlofluanid, (4-2) tolylfluanid.

Emphasis is given to the active compound combinations C listed in table 3 below:

TABLE 3

Active compound combinations C

| No. | Carboxamide of the formula (I) | Sulfenamide (group 4) |
| --- | --- | --- |
| C-1 | (1-1) N-[2-(1,3-dimethylbutyl)-3-thienyl]-1-methyl-3-(trifluoromethyl)-1H-pyrazole-4-carboxamide | (4-1) dichlofluanid |
| C-2 | (1-1) N-[2-(1,3-dimethylbutyl)-3-thienyl]-1-methyl-3-(trifluoromethyl)-1H-pyrazole-4-carboxamide | (4-2) tolylfluanid |
| C-3 | (1-9) N-[2-(1,3-dimethylbutyl)-3-thienyl]-5-fluoro-1,3-dimethyl-1H-pyrazole-4-carboxamide | (4-1) dichlofluanid |

TABLE 3-continued

Active compound combinations C

| No. | Carboxamide of the formula (I) | Sulfenamide (group 4) |
|---|---|---|
| C-4 | (1-9) N-[2-(1,3-dimethylbutyl)-3-thienyl]-5-fluoro-1,3-dimethyl-1H-pyrazole-4-carboxamide | (4-2) tolylfluanid |
| C-5 | (1-13) N-[2-(1,3-dimethylbutyl)-3-thienyl]-1-methyl-4-(trifluoromethyl)-1H-pyrrole-3-carboxamide | (4-1) dichlofluanid |
| C-6 | (1-13) N-[2-(1,3-dimethylbutyl)-3-thienyl]-1-methyl-4-(trifluoromethyl)-1H-pyrrole-3-carboxamide | (4-2) tolylfluanid |
| C-7 | (1-25) N-[2-(1,3-dimethylbutyl)-3-thienyl]-2-methyl-4-(trifluoromethyl)-1,3-thiazole-5-carboxamide | (4-1) dichlofluanid |
| C-8 | (1-25) N-[2-(1,3-dimethylbutyl)-3-thienyl]-2-methyl-4-(trifluoromethyl)-1,3-thiazole-5-carboxamide | (4-2) tolylfluanid |

Preference is given to active compound combinations D in which the valinamide (group 5) is selected from the following list: (5-1) iprovalicarb, (5-3) benthiavalicarb.

Emphasis is given to the active compound combinations D listed in table 4 below:

TABLE 4

Active compound combinations D

| No. | Carboxamide of the formula (I) | Valinamide (group 5) |
|---|---|---|
| D-1 | (1-1) N-[2-(1,3-dimethylbutyl)-3-thienyl]-1-methyl-3-(trifluoromethyl)-1H-pyrazole-4-carboxamide | (5-1) iprovalicarb |
| D-2 | (1-1) N-[2-(1,3-dimethylbutyl)-3-thienyl]-1-methyl-3-(trifluoromethyl)-1H-pyrazole-4-carboxamide | (5-2) benthiavalicarb |
| D-3 | (1-9) N-[2-(1,3-dimethylbutyl)-3-thienyl]-5-fluoro-1,3-dimethyl-1H-pyrazole-4-carboxamide | (5-1) iprovalicarb |
| D-4 | (1-9) N-[2-(1,3-dimethylbutyl)-3-thienyl]-5-fluoro-1,3-dimethyl-1H-pyrazole-4-carboxamide | (5-2) benthiavalicarb |
| D-5 | (1-13) N-[2-(1,3-dimethylbutyl)-3-thienyl]-1-methyl-4-(trifluoromethyl)-1H-pyrrole-3-carboxamide | (5-1) iprovalicarb |
| D-6 | (1-13) N-[2-(1,3-dimethylbutyl)-3-thienyl]-1-methyl-4-(trifluoromethyl)-1H-pyrrole-3-carboxamide | (5-2) benthiavalicarb |
| D-7 | (1-25) N-[2-(1,3-dimethylbutyl)-3-thienyl]-2-methyl-4-(trifluoromethyl)-1,3-thiazole-5-carboxamide | (5-1) iprovalicarb |
| D-8 | (1-25) N-[2-(1,3-dimethylbutyl)-3-thienyl]-2-methyl-4-(trifluoromethyl)-1,3-thiazole-5-carboxamide | (5-2) benthiavalicarb |

Preference is given to active compound combinations E in which the carboxamide (group 6) is selected from the list below: (6-1) 2-chloro-N-(1,1,3-trimethylindan-4-yl)nicotinamide, (6-2) boscalid, (6-3) furametpyr, (6-4) ethaboxam, (6-5) fenhexamid, (6-6) carpropamid, (6-7) 2-chloro-4-(2-fluoro-2-methylpropionylamino)-N,N-dimethylbenzamide, (6-8) picobenzamid, (6-9) zoxamide, (6-10) 3,4-dichloro-N-(2-cyanophenyl)isothiazole-5-carboxamide, (6-11) carboxin, (6-12) tiadinil, (6-13) silthiofam.

Particular preference is given to active compound combinations E in which the carboxamide (group 6) is selected from the list below: (6-2) boscalid, (6-4) ethaboxam, (6-5) fenhexamid, (6-6) carpropamid, (6-7) 2-chloro-4-(2-fluoro-2-methylpropionylamino)-N,N-dimethylbenzamide, (6-8) picobenzamid, (6-9) zoxamide, (6-10) 3,4-dichloro-N-(2-cyanophenyl)isothiazole-5-carboxamide.

Very particular preference is given to active compound combinations E in which the carboxamide (group 6) is selected from the following list: (6-2) boscalid, (6-5) fenhexamid, (6-6) carpropamid, (6-8) picobenzamid.

Emphasis is given to the active compound combinations E listed in table 5 below:

TABLE 5

Active compound combinations E

| No. | Carboxamide of the formula (I) | Carboxamide (group 6) |
|---|---|---|
| E-1 | (1-1) N-[2-(1,3-dimethylbutyl)-3-thienyl]-1-methyl-3-(trifluoromethyl)-1H-pyrazole-4-carboxamide | (6-2) boscalid |
| E-2 | (1-1) N-[2-(1,3-dimethylbutyl)-3-thienyl]-1-methyl-3-(trifluoromethyl)-1H-pyrazole-4-carboxamide | (6-5) fenhexamid |
| E-3 | (1-1) N-[2-(1,3-dimethylbutyl)-3-thienyl]-1-methyl-3-(trifluoromethyl)-1H-pyrazole-4-carboxamide | (6-6) carpropamid |
| E-4 | (1-1) N-[2-(1,3-dimethylbutyl)-3-thienyl]-1-methyl-3-(trifluoromethyl)-1H-pyrazole-4-carboxamide | (6-8) picobenzamid |
| E-5 | (1-9) N-[2-(1,3-dimethylbutyl)-3-thienyl]-5-fluoro-1,3-dimethyl-1H-pyrazole-4-carboxamide | (6-2) boscalid |
| E-6 | (1-9) N-[2-(1,3-dimethylbutyl)-3-thienyl]-5-fluoro-1,3-dimethyl-1H-pyrazole-4-carboxamide | (6-5) fenhexamid |

TABLE 5-continued

Active compound combinations E

| No. | Carboxamide of the formula (I) | Carboxamide (group 6) |
|---|---|---|
| E-7 | (1-9) N-[2-(1,3-dimethylbutyl)-3-thienyl]-5-fluoro-1,3-dimethyl-1H-pyrazole-4-carboxamide | (6-6) carpropamid |
| E-8 | (1-9) N-[2-(1,3-dimethylbutyl)-3-thienyl]-5-fluoro-1,3-dimethyl-1H-pyrazole-4-carboxamide | (6-8) picobenzamid |
| E-9 | (1-13) N-[2-(1,3-dimethylbutyl)-3-thienyl]-1-methyl-4-(trifluoromethyl)-1H-pyrrole-3-carboxamide | (6-2) boscalid |
| E-10 | (1-13) N-[2-(1,3-dimethylbutyl)-3-thienyl]-1-methyl-4-(trifluoromethyl)-1H-pyrrole-3-carboxamide | (6-5) fenhexamid |
| E-11 | (1-13) N-[2-(1,3-dimethylbutyl)-3-thienyl]-1-methyl-4-(trifluoromethyl)-1H-pyrrole-3-carboxamide | (6-6) carpropamid |
| E-12 | (1-13) N-[2-(1,3-dimethylbutyl)-3-thienyl]-1-methyl-4-(trifluoromethyl)-1H-pyrrole-3-carboxamide | (6-8) picobenzamid |
| E-13 | (1-25) N-[2-(1,3-dimethylbutyl)-3-thienyl]-2-methyl-4-(trifluoromethyl)-1,3-thiazole-5-carboxamide | (6-2) boscalid |
| E-14 | (1-25) N-[2-(1,3-dimethylbutyl)-3-thienyl]-2-methyl-4-(trifluoromethyl)-1,3-thiazole-5-carboxamide | (6-5) fenhexamid |
| E-15 | (1-25) N-[2-(1,3-dimethylbutyl)-3-thienyl]-2-methyl-4-(trifluoromethyl)-1,3-thiazole-5-carboxamide | (6-6) carpropamid |
| E-16 | (1-25) N-[2-(1,3-dimethylbutyl)-3-thienyl]-2-methyl-4-(trifluoromethyl)-1,3-thiazole-5-carboxamide | (6-8) picobenzamid |

Preference is given to active compound combinations F in which the dithiocarbamate (group 7) is selected from the following list: (7-1) mancozeb, (7-2) maneb, (7-4) propineb, (7-5) thiram, (7-6) zineb.

Particular preference is given to active compound combinations F in which the dithiocarbamate (group 7) is selected from the following list: (7-1) mancozeb, (7-4) propineb.

Emphasis is given to the active compound combinations F listed in table 6 below:

TABLE 6

Active compound combinations F

| No. | Carboxamide of the formula (I) | Dithiocarbamate (group 7) |
|---|---|---|
| F-1 | (1-1) N-[2-(1,3-dimethylbutyl)-3-thienyl]-1-methyl-3-(trifluoromethyl)-1H-pyrazole-4-carboxamide | (7-1) mancozeb |
| F-2 | (1-1) N-[2-(1,3-dimethylbutyl)-3-thienyl]-1-methyl-3-(trifluoromethyl)-1H-pyrazole-4-carboxamide | (7-4) propineb |
| F-3 | (1-9) N-[2-(1,3-dimethylbutyl)-3-thienyl]-5-fluoro-1,3-dimethyl-1H-pyrazole-4-carboxamide | (7-1) mancozeb |
| F-4 | (1-9) N-[2-(1,3-dimethylbutyl)-3-thienyl]-5-fluoro-1,3-dimethyl-1H-pyrazole-4-carboxamide | (7-4) propineb |
| F-5 | (1-13) N-[2-(1,3-dimethylbutyl)-3-thienyl]-1-methyl-4-(trifluoromethyl)-1H-pyrrole-3-carboxamide | (7-1) mancozeb |
| F-6 | (1-13) N-[2-(1,3-dimethylbutyl)-3-thienyl]-1-methyl-4-(trifluoromethyl)-1H-pyrrole-3-carboxamide | (7-4) propineb |
| F-7 | (1-25) N-[2-(1,3-dimethylbutyl)-3-thienyl]-2-methyl-4-(trifluoromethyl)-1,3-thiazole-5-carboxamide | (7-1) mancozeb |
| F-8 | (1-25) N-[2-(1,3-dimethylbutyl)-3-thienyl]-2-methyl-4-(trifluoromethyl)-1,3-thiazole-5-carboxamide | (7-4) propineb |

Preference is given to active compound combinations G in which the acylalanine (group 8) is selected from the following list: (8-1) benalaxyl, (8-2) furalaxyl, (8-5) benalaxyl-M.

Particular preference is given to active compound combinations G in which the acylalanine of the formula (VI) (group 8) is selected from the following list: (8-5) benalaxyl-M.

Emphasis is given to the active compound combinations G listed in table 7 below:

TABLE 7

Active compound combinations G

| No. | Carboxamide of the formula (I) | Acylalanine (group 8) |
|---|---|---|
| G-1 | (1-1) N-[2-(1,3-dimethylbutyl)-3-thienyl]-1-methyl-3-(trifluoromethyl)-1H-pyrazole-4-carboxamide | (8-5) benalaxyl-M |
| G-2 | (1-9) N-[2-(1,3-dimethylbutyl)-3-thienyl]-5-fluoro-1,3-dimethyl-1H-pyrazole-4-carboxamide | (8-5) benalaxyl-M |
| G-3 | (1-13) N-[2-(1,3-dimethylbutyl)-3-thienyl]-1-methyl-4-(trifluoromethyl)-1H-pyrrole-3-carboxamide | (8-5) benalaxyl-M |

TABLE 7-continued

Active compound combinations G

| No. | Carboxamide of the formula (I) | Acylalanine (group 8) |
|---|---|---|
| G-4 | (1-25) N-[2-(1,3-dimethylbutyl)-3-thienyl]-2-methyl-4-(trifluoromethyl)-1,3-thiazole-5-carboxamide | (8-5) benalaxyl-M |

Preference is given to active compound combinations H in which the anilinopyrimidine (group 9) is selected from the following list: (9-1) cyprodinil, (9-2) pyrimethanil.

Emphasis is given to the active compound combinations H listed in table 8 below:

TABLE 8

Active compound combinations H

| No. | Carboxamide of the formula (I) | Anilinopyrimidine (group 9) |
|---|---|---|
| H-1 | (1-1) N-[2-(1,3-dimethylbutyl)-3-thienyl]-1-methyl-3-(trifluoromethyl)-1H-pyrazole-4-carboxamide | (9-1) cyprodinil |
| H-2 | (1-1) N-[2-(1,3-dimethylbutyl)-3-thienyl]-1-methyl-3-(trifluoromethyl)-1H-pyrazole-4-carboxamide | (9-2) pyrimethanil |
| H-3 | (1-9) N-[2-(1,3-dimethylbutyl)-3-thienyl]-5-fluoro-1,3-dimethyl-1H-pyrazole-4-carboxamide | (9-1) cyprodinil |
| H-4 | (1-9) N-[2-(1,3-dimethylbutyl)-3-thienyl]-5-fluoro-1,3-dimethyl-1H-pyrazole-4-carboxamide | (9-2) pyrimethanil |
| H-5 | (1-13) N-[2-(1,3-dimethylbutyl)-3-thienyl]-1-methyl-4-(trifluoromethyl)-1H-pyrrole-3-carboxamide | (9-1) cyprodinil |
| H-6 | (1-13) N-[2-(1,3-dimethylbutyl)-3-thienyl]-1-methyl-4-(trifluoromethyl)-1H-pyrrole-3-carboxamide | (9-2) pyrimethanil |
| H-7 | (1-25) N-[2-(1,3-dimethylbutyl)-3-thienyl]-2-methyl-4-(trifluoromethyl)-1,3-thiazole-5-carboxamide | (9-1) cyprodinil |
| H-8 | (1-25) N-[2-(1,3-dimethylbutyl)-3-thienyl]-2-methyl-4-(trifluoromethyl)-1,3-thiazole-5-carboxamide | (9-2) pyrimethanil |

Preference is given to active compound combinations I in which the benzimidazole (group 10) is selected from the following list: (10-1) 6-chloro-5-[(3,5-dimethylisoxazol-4-yl)sulfonyl]-2,2-difluoro-5H-[1,3]dioxolo-[4,5-f]benzimidazole, (10-2) benomyl, (10-3) carbendazim, (10-4) chlorfenazole, (10-5) fuberidazole, (10-6) thiabendazole.

Particular preference is given to active compound combinations I in which the benzimidazole of the formula (VIII) (group 10) is: (10-3) carbendazim.

Emphasis is given to the active compound combinations I listed in table 9 below:

TABLE 9

Active compound combinations I

| No. | Carboxamide of the formula (I) | Benzimidazole (group 10) |
|---|---|---|
| I-1 | (1-1) N-[2-(1,3-dimethylbutyl)-3-thienyl]-1-methyl-3-(trifluoromethyl)-1H-pyrazole-4-carboxamide | (10-3) carbendazim |
| I-2 | (1-9) N-[2-(1,3-dimethylbutyl)-3-thienyl]-5-fluoro-1,3-dimethyl-1H-pyrazole-4-carboxamide | (10-3) carbendazim |
| I-3 | (1-13) N-[2-(1,3-dimethylbutyl)-3-thienyl]-1-methyl-4-(trifluoromethyl)-1H-pyrrole-3-carboxamide | (10-3) carbendazim |
| I-4 | (1-25) N-[2-(1,3-dimethylbutyl)-3-thienyl]-2-methyl-4-(trifluoromethyl)-1,3-thiazole-5-carboxamide | (10-3) carbendazim |

Preference is given to active compound combinations J in which the carbamate (group 11) is selected from the list below: (11-1) propamocarb, (11-2) propamocarb hydrochloride, (11-3) propamocarb-fosetyl.

Emphasis is given to the active compound combinations J listed in table 10 below:

TABLE 10

Active compound combinations J

| Nr. | Carboxamide of the formula (I) | Carbamate (group 11) |
|---|---|---|
| J-1 | (1-1) N-[2-(1,3-dimethylbutyl)-3-thienyl]-1-methyl-3-(trifluoromethyl)-1H-pyrazole-4-carboxamide | (11-1) propamocarb |
| J-2 | (1-1) N-[2-(1,3-dimethylbutyl)-3-thienyl]-1-methyl-3-(trifluoromethyl)-1H-pyrazole-4-carboxamide | (11-2) propamocarb hydrochloride |
| J-3 | (1-1) N-[2-(1,3-dimethylbutyl)-3-thienyl]-1-methyl-3-(trifluoromethyl)-1H-pyrazole-4-carboxamide | (11-3) propamocarb-fosetyl |
| J-4 | (1-9) N-[2-(1,3-dimethylbutyl)-3-thienyl]-5-fluoro-1,3-dimethyl-1H-pyrazole-4-carboxamide | (11-1) propamocarb |
| J-5 | (1-9) N-[2-(1,3-dimethylbutyl)-3-thienyl]-5-fluoro-1,3-dimethyl-1H-pyrazole-4-carboxamide | (11-2) propamocarb hydrochloride |
| J-6 | (1-9) N-[2-(1,3-dimethylbutyl)-3-thienyl]-5-fluoro-1,3-dimethyl-1H-pyrazole-4-carboxamide | (11-3) propamocarb-fosetyl |
| J-7 | (1-13) N-[2-(1,3-dimethylbutyl)-3-thienyl]-1-methyl-4-(trifluoromethyl)-1H-pyrrole-3-carboxamide | (11-1) propamocarb |
| J-8 | (1-13) N-[2-(1,3-dimethylbutyl)-3-thienyl]-1-methyl-4-(trifluoromethyl)-1H-pyrrole-3-carboxamide | (11-2) propamocarb hydrochloride |
| J-9 | (1-13) N-[2-(1,3-dimethylbutyl)-3-thienyl]-1-methyl-4-(trifluoromethyl)-1H-pyrrole-3-carboxamide | (11-3) propamocarb-fosetyl |
| J-10 | (1-25) N-[2-(1,3-dimethylbutyl)-3-thienyl]-2-methyl-4-(trifluoromethyl)-1,3-thiazole-5-carboxamide | (11-1) propamocarb |
| J-11 | (1-25) N-[2-(1,3-dimethylbutyl)-3-thienyl]-2-methyl-4-(trifluoromethyl)-1,3-thiazole-5-carboxamide | (11-2) propamocarb hydrochloride |
| J-12 | (1-25) N-[2-(1,3-dimethylbutyl)-3-thienyl]-2-methyl-4-(trifluoromethyl)-1,3-thiazole-5-carboxamide | (11-3) propamocarb-fosetyl |

Preference is given to active compound combinations K in which the dicarboximide (group 12) is selected from the list below: (12-2) folpet, (12-3) iprodione.

Emphasis is given to the active compound combinations K listed in table 11 below:

TABLE 11

Active compound combinations K

| No. | Carboxamide of the formula (I) | Dicarboximide (group 12) |
|---|---|---|
| K-1 | (1-1) N-[2-(1,3-dimethylbutyl)-3-thienyl]-1-methyl-3-(trifluoromethyl)-1H-pyrazole-4-carboxamide | (12-2) folpet |
| K-2 | (1-1) N-[2-(1,3-dimethylbutyl)-3-thienyl]-1-methyl-3-(trifluoromethyl)-1H-pyrazole-4-carboxamide | (12-3) iprodione |
| K-3 | (1-9) N-[2-(1,3-dimethylbutyl)-3-thienyl]-5-fluoro-1,3-dimethyl-1H-pyrazole-4-carboxamide | (12-2) folpet |
| K-4 | (1-9) N-[2-(1,3-dimethylbutyl)-3-thienyl]-5-fluoro-1,3-dimethyl-1H-pyrazole-4-carboxamide | (12-3) iprodione |
| K-5 | (1-13) N-[2-(1,3-dimethylbutyl)-3-thienyl]-1-methyl-4-(trifluoromethyl)-1H-pyrrole-3-carboxamide | (12-2) folpet |
| K-6 | (1-13) N-[2-(1,3-dimethylbutyl)-3-thienyl]-1-methyl-4-(trifluoromethyl)-1H-pyrrole-3-carboxamide | (12-3) iprodione |
| K-7 | (1-25) N-[2-(1,3-dimethylbutyl)-3-thienyl]-2-methyl-4-(trifluoromethyl)-1,3-thiazole-5-carboxamide | (12-2) folpet |
| K-8 | (1-25) N-[2-(1,3-dimethylbutyl)-3-thienyl]-2-methyl-4-(trifluoromethyl)-1,3-thiazole-5-carboxamide | (12-3) iprodione |

Preference is given to active compound combinations L in which the guanidine (group 13) is selected from the list below: (13-1) dodine, (13-2) guazatine.

Emphasis is given to the active compound combinations L listed in table 12 below:

TABLE 12

Active compound combinations L

| No. | Carboxamide of the formula (I) | Guanidine (group 13) |
|---|---|---|
| L-1 | (1-1) N-[2-(1,3-dimethylbutyl)-3-thienyl]-1-methyl-3-(trifluoromethyl)-1H-pyrazole-4-carboxamide | (13-1) dodine |
| L-2 | (1-1) N-[2-(1,3-dimethylbutyl)-3-thienyl]-1-methyl-3-(trifluoromethyl)-1H-pyrazole-4-carboxamide | (13-2) guazatine |

TABLE 12-continued

Active compound combinations L

| No. | Carboxamide of the formula (I) | Guanidine (group 13) |
| --- | --- | --- |
| L-3 | (1-9) N-[2-(1,3-dimethylbutyl)-3-thienyl]-5-fluoro-1,3-dimethyl-1H-pyrazole-4-carboxamide | (13-1) dodine |
| L-4 | (1-9) N-[2-(1,3-dimethylbutyl)-3-thienyl]-5-fluoro-1,3-dimethyl-1H-pyrazole-4-carboxamide | (13-2) guazatine |
| L-5 | (1-13) N-[2-(1,3-dimethylbutyl)-3-thienyl]-1-methyl-4-(trifluoromethyl)-1H-pyrrole-3-carboxamide | (13-1) dodine |
| L-6 | (1-13) N-[2-(1,3-dimethylbutyl)-3-thienyl]-1-methyl-4-(trifluoromethyl)-1H-pyrrole-3-carboxamide | (13-2) guazatine |
| L-7 | (1-25) N-[2-(1,3-dimethylbutyl)-3-thienyl]-2-methyl-4-(trifluoromethyl)-1,3-thiazole-5-carboxamide | (13-1) dodine |
| L-8 | (1-25) N-[2-(1,3-dimethylbutyl)-3-thienyl]-2-methyl-4-(trifluoromethyl)-1,3-thiazole-5-carboxamide | (13-2) guazatine |

Preference is given to active compound combinations M in which the imidazole (group 14) is selected from the list below: (14-2) prochloraz, (14-3) triazoxide.

Emphasis is given to the active compound combinations M listed in table 13 below:

TABLE 13

Active compound combinations M

| No. | Carboxamide of the formula (I) | Imidazole (group 14) |
| --- | --- | --- |
| M-1 | (1-1) N-[2-(1,3-dimethylbutyl)-3-thienyl]-1-methyl-3-(trifluoromethyl)-1H-pyrazole-4-carboxamide | (14-2) prochloraz |
| M-2 | (1-1) N-[2-(1,3-dimethylbutyl)-3-thienyl]-1-methyl-3-(trifluoromethyl)-1H-pyrazole-4-carboxamide | (14-3) triazoxide |
| M-3 | (1-9) N-[2-(1,3-dimethylbutyl)-3-thienyl]-5-fluoro-1,3-dimethyl-1H-pyrazole-4-carboxamide | (14-2) prochloraz |
| M-4 | (1-9) N-[2-(1,3-dimethylbutyl)-3-thienyl]-5-fluoro-1,3-dimethyl-1H-pyrazole-4-carboxamide | (14-3) triazoxide |
| M-5 | (1-13) N-[2-(1,3-dimethylbutyl)-3-thienyl]-1-methyl-4-(trifluoromethyl)-1H-pyrrole-3-carboxamide | (14-2) prochloraz |
| M-6 | (1-13) N-[2-(1,3-dimethylbutyl)-3-thienyl]-1-methyl-4-(trifluoromethyl)-1H-pyrrole-3-carboxamide | (14-3) triazoxide |
| M-7 | (1-25) N-[2-(1,3-dimethylbutyl)-3-thienyl]-2-methyl-4-(trifluoromethyl)-1,3-thiazole-5-carboxamide | (14-2) prochloraz |
| M-8 | (1-25) N-[2-(1,3-dimethylbutyl)-3-thienyl]-2-methyl-4-(trifluoromethyl)-1,3-thiazole-5-carboxamide | (14-3) triazoxide |

Preference is given to active compound combinations N in which the morpholine (group 15) is selected from the following list: (15-1) aldimorph, (15-2) tridemorph, (15-3) dodemorph, (15-4) fenpropimorph.

Particular preference is given to active compound combinations N in which the morpholine (group 15) is selected from the list below: (15-4) fenpropimorph.

Emphasis is given to the active compound combinations N listed in table 14 below:

Preference is given to active compound combinations O in which the fungicide (group 19) is selected from the list below: (19-1) acibenzolar-5-methyl, (19-3) famoxadone, (19-4) oxadixyl, (19-5) spiroxamine, (19-8) fenamidone, (19-14) N-({4-[(cyclopropylamino)carbonyl]phenyl}sulfonyl)-2-methoxybenzamide, (19-15) 2-(4-chlorophenyl)-N-{2-[3-methoxy-4-(prop-2-yn-1-yloxy)phenyl]-ethyl}-2-(prop-2-yn-1-yloxy)acetamide.

Particular preference is given to active compound combinations O in which the fungicide (group 19) is selected from the list below: (19-5) spiroxamine, (19-14) N-({4-[(cyclopropylamino)carbonyl]-phenyl}sulfonyl)-2-methoxybenzamide, (19-15) 2-(4-chlorophenyl)-N-{2-[3-methoxy-4-

TABLE 14

Active compound combinations N

| No. | Carboxamide of the formula (I) | Morpholine (group 15) |
| --- | --- | --- |
| N-1 | (1-1) N-[2-(1,3-dimethylbutyl)-3-thienyl]-1-methyl-3-(trifluoromethyl)-1H-pyrazole-4-carboxamide | (15-4) fenpropimorph |
| N-2 | (1-9) N-[2-(1,3-dimethylbutyl)-3-thienyl]-5-fluoro-1,3-dimethyl-1H-pyrazole-4-carboxamide | (15-4) fenpropimorph |
| N-3 | (1-13) N-[2-(1,3-dimethylbutyl)-3-thienyl]-1-methyl-4-(trifluoromethyl)-1H-pyrrole-3-carboxamide | (15-4) fenpropimorph |
| N-4 | (1-25) N-[2-(1,3-dimethylbutyl)-3-thienyl]-2-methyl-4-(trifluoromethyl)-1,3-thiazole-5-carboxamide | (15-4) fenpropimorph |

(prop-2-yn-1-yloxy)phenyl]ethyl}-2-(prop-2-yn-1-yloxy)acetamide.

Emphasis is given to the active compound combinations O listed in table 15 below:

TABLE 15

Active compound combinations O

| No. | Carboxamide of the formula (I) | Fungicide (group 19) |
| --- | --- | --- |
| O-1 | (1-1) N-[2-(1,3-dimethylbutyl)-3-thienyl]-1-methyl-3-(trifluoromethyl)-1H-pyrazole-4-carboxamide | (19-5) spiroxamine |
| O-2 | (1-1) N-[2-(1,3-dimethylbutyl)-3-thienyl]-1-methyl-3-(trifluoromethyl)-1H-pyrazole-4-carboxamide | (19-14) N-({4-[(cyclopropylamino)-carbonyl]phenyl}sulfonyl)-2-methoxy-benzamide |
| O-3 | (1-1) N-[2-(1,3-dimethylbutyl)-3-thienyl]-1-methyl-3-(trifluoromethyl)-1H-pyrazole-4-carboxamide | (19-15) 2-(4-chlorophenyl)-N-{2-[3-methoxy-4-(prop-2-yn-1-yloxy)phenyl]-ethyl}-2-(prop-2-yn-1-yloxy)acetamide |
| O-4 | (1-9) N-[2-(1,3-dimethylbutyl)-3-thienyl]-5-fluoro-1,3-dimethyl-1H-pyrazole-4-carboxamide | (19-5) spiroxamine |
| O-5 | (1-9) N-[2-(1,3-dimethylbutyl)-3-thienyl]-5-fluoro-1,3-dimethyl-1H-pyrazole-4-carboxamide | (19-14) N-({4-[(cyclopropylamino)-carbonyl]phenyl}sulfonyl)-2-methoxy-benzamide |
| O-6 | (1-9) N-[2-(1,3-dimethylbutyl)-3-thienyl]-5-fluoro-1,3-dimethyl-1H-pyrazole-4-carboxamide | (19-15) 2-(4-chlorophenyl)-N-{2-[3-methoxy-4-(prop-2-yn-1-yloxy)phenyl]-ethyl}-2-(prop-2-yn-1-yloxy)acetamide |
| O-7 | (1-13) N-[2-(1,3-dimethylbutyl)-3-thienyl]-1-methyl-4-(trifluoromethyl)-1H-pyrrole-3-carboxamide | (19-5) spiroxamine |
| O-8 | (1-13) N-[2-(1,3-dimethylbutyl)-3-thienyl]-1-methyl-4-(trifluoromethyl)-1H-pyrrole-3-carboxamide | (19-14) N-({4-[(cyclopropylamino)-carbonyl]phenyl}sulfonyl)-2-methoxy-benzamide |
| O-9 | (1-13) N-[2-(1,3-dimethylbutyl)-3-thienyl]-1-methyl-4-(trifluoromethyl)-1H-pyrrole-3-carboxamide | (19-15) 2-(4-chlorophenyl)-N-{2-[3-methoxy-4-(prop-2-yn-1-yloxy)phenyl]-ethyl}-2-(prop-2-yn-1-yloxy)acetamide |
| O-10 | (1-25) N-[2-(1,3-dimethylbutyl)-3-thienyl]-2-methyl-4-(trifluoromethyl)-1,3-thiazole-5-carboxamide | (19-5) spiroxamine |
| O-11 | (1-25) N-[2-(1,3-dimethylbutyl)-3-thienyl]-2-methyl-4-(trifluoromethyl)-1,3-thiazole-5-carboxamide | (19-14) N-({4-[cyclopropylamino)-carbonyl]phenyl}sulfonyl)-2-methoxy-benzamide |
| O-12 | (1-25) N-[2-(1,3-dimethylbutyl)-3-thienyl]-2-methyl-4-(trifluoromethyl)-1,3-thiazole-5-carboxamide | (19-15) 2-(4-chlorophenyl)-N-{2-[3-methoxy-4-(prop-2-yn-1-yloxy)phenyl]-ethyl}-2-(prop-2-yn-1-yloxy)acetamide |

Preference is given to the active compound combinations P in which the (thio)urea derivative (group 20) is selected from the list below: (20-1) pencycuron.

Emphasis is given to the active compound combinations P listed in table 16 below:

TABLE 16

Active compound combinations P

| No. | Carboxamide of the formula (I) | (Thio)urea derivative (group 20) |
| --- | --- | --- |
| P-1 | (1-1) N-[2-(1,3-dimethylbutyl)-3-thienyl]-1-methyl-3-(trifluoromethyl)-1H-pyrazole-4-carboxamide | (20-1) pencycuron |
| P-2 | (1-9) N-[2-(1,3-dimethylbutyl)-3-thienyl]-5-fluoro-1,3-dimethyl-1H-pyrazole-4-carboxamide | (20-1) pencycuron |
| P-3 | (1-13) N-[2-(1,3-dimethylbutyl)-3-thienyl]-1-methyl-4-(trifluoromethyl)-1H-pyrrole-3-carboxamide | (20-1) pencycuron |
| P-4 | (1-25) N-[2-(1,3-dimethylbutyl)-3-thienyl]-2-methyl-4-(trifluoromethyl)-1,3-thiazole-5-carboxamide | (20-1) pencycuron |

Preference is given to active compound combinations Q in which the triazolopyrimidine (group 22) is selected from the list below: (22-1) 5-chloro-N-[(1S)-2,2,2-trifluoro-1-methylethyl]-6-(2,4,6-trifluorophenyl)[1,2,4]triazolo[1,5-a]pyrimidine-7-amine, (22-2) 5-chloro-N-[(1R)-1,2-dimethylpropyl]-6-(2,4,6-trifluorophenyl)[1,2,4]triazolo[1,5-a]pyrimidine-7-amine, (22-3) 5-chloro-6-(2-chloro-6-fluorophenyl)-7-(4-methylpiperidin-1-yl)[1,2,4]triazolo[1,5-a]pyrimidine, (22-4) 5-chloro-6-(2,4,6-trifluorophenyl)-7-(4-methylpiperidin-1-yl)[1,2,4]triazolo[1,5-a]pyrimidine.

Particular preference is given to active compound combinations Q in which the triazolopyrimidine (group 22) is selected from the list below: (22-1) 5-chloro-N-[(1S)-2,2,2-trifluoro-1-methylethyl]-6-(2,4,6-trifluorophenyl)[1,2,4]triazolo[1,5-a]pyrimidine-7-amine, (22-2) 5-chloro-N-[(1R)-1,2-dimethylpropyl]-6-(2,4,6-trifluorophenyl)[1,2,4]triazolo[1,5-a]pyrimidine-7-amine, (22-4) 5-chloro-6-(2,4,6-trifluorophenyl)-7-(4-methylpiperidin-1-yl)[1,2,4]triazolo[1,5-a]pyrimidine, (22-5) 5-chloro-6-(2,4,6-trifluorophenyl)-N-[(1S)-1,2,2-trimethylpropyl][1,2,4]triazolo[1,5-a]pyrimidine-7-amine.

Emphasis is given to the active compound combinations Q listed in table 17 below:

TABLE 17

Active compound combinations Q

| No. | Carboxamide of the formula (I) | Triazolopyrimidine (group 22) |
|---|---|---|
| Q-1 | (1-1) N-[2-(1,3-dimethylbutyl)-3-thienyl]-1-methyl-3-(trifluoromethyl)-1H-pyrazole-4-carboxamide | (22-1) 5-chloro-N-[(1S)-2,2,2-trifluoro-1-methylethyl]-6-(2,4,6-trifluorophenyl)-[1,2,4]triazolo[1,5-a]pyrimidine-7-amine |
| Q-2 | (1-1) N-[2-(1,3-dimethylbutyl)-3-thienyl]-1-methyl-3-(trifluoromethyl)-1H-pyrazole-4-carboxamide | (22-2) 5-chloro-N-[(1R)-1,2-dimethylpropyl]-6-(2,4,6-trifluorophenyl)[1,2,4]triazolo-[1,5-a]pyrimidine-7-amine |
| Q-3 | (1-1) N-[2-(1,3-dimethylbutyl)-3-thienyl]-1-methyl-3-(trifluoromethyl)-1H-pyrazole-4-carboxamide | (22-4) 5-chloro-6-(2,4,6-trifluorophenyl)-7-(4-methylpiperidin-1-yl)[1,2,4]triazolo[1,5-a]-pyrimidine |
| Q-4 | (1-1) N-[2-(1,3-dimethylbutyl)-3-thienyl]-1-methyl-3-(trifluoromethyl)-1H-pyrazole-4-carboxamide | (22-5) 5-chloro-6-(2,4,6-trifluorophenyl)-N-[(1S)-1,2,2-trimethylpropyl][1,2,4]triazolo-[1,5-a]pyrimidine-7-amine |
| Q-5 | (1-9) N-[2-(1,3-dimethylbutyl)-3-thienyl]-5-fluoro-1,3-dimethyl-1H-pyrazole-4-carboxamide | (22-1) 5-chloro-N-[(1S)-2,2,2-trifluoro-1-methylethyl]-6-(2,4,6-trifluorophenyl)-[1,2,4]triazolo[1,5-a]pyrimidine-7-amine |
| Q-6 | (1-9) N-[2-(1,3-dimethylbutyl)-3-thienyl]-5-fluoro-1,3-dimethyl-1H-pyrazole-4-carboxamide | (22-2) 5-chloro-N-[(1R)-1,2-dimethylpropyl]-6-(2,4,6-trifluorophenyl)[1,2,4]triazolo-[1,5-a]pyrimidine-7-amine |
| Q-7 | (1-9) N-[2-(1,3-dimethylbutyl)-3-thienyl]-5-fluoro-1,3-dimethyl-1H-pyrazole-4-carboxamide | (22-4) 5-chloro-6-(2,4,6-trifluorophenyl)-7-(4-methylpiperidin-1-yl)[1,2,4]triazolo[1,5-a]-pyrimidine |
| Q-8 | (1-9) N-[2-(1,3-dimethylbutyl)-3-thienyl]-5-fluoro-1,3-dimethyl-1H-pyrazole-4-carboxamide | (22-5) 5-chloro-6-(2,4,6-trifluorophenyl)-N-[(1S)-1,2,2-trimethylpropyl][1,2,4]triazolo-[1,5-a]pyrimidine-7-amine |
| Q-9 | (1-13) N-[2-(1,3-dimethylbutyl)-3-thienyl]-1-methyl-4-(trifluoromethyl)-1H-pyrrole-3-carboxamide | (22-1) 5-chloro-N-[(1S)-2,2,2-trifluoro-1-methylethyl]-6-(2,4,6-trifluorophenyl)-[1,2,4]triazolo[1,5-a]pyrimidine-7-amine |
| Q-10 | (1-13) N-[2-(1,3-dimethylbutyl)-3-thienyl]-1-methyl-4-(trifluoromethyl)-1H-pyrrole-3-carboxamide | (22-2) 5-chloro-N-[(1R)-1,2-dimethylpropyl]-6-(2,4,6-trifluorophenyl)[1,2,4]triazolo-[1,5-a]pyrimidine-7-amine |
| Q-11 | (1-13) N-[2-(1,3-dimethylbutyl)-3-thienyl]-1-methyl-4-(trifluoromethyl)-1H-pyrrole-3-carboxamide | (22-4) 5-chloro-6-(2,4,6-trifluorphenyl)-7-(4-methylpiperidin-1-yl)[1,2,4]triazolo[1,5-a]-pyrimidine |
| Q-12 | (1-13) N-[2-(1,3-dimethylbutyl)-3-thienyl]-1-methyl-4-(trifluoromethyl)-1H-pyrrole-3-carboxamide | (22-5) 5-chloro-6-(2,4,6-trifluorphenyl)-N-[(1S)-1,2,2-trimethylpropyl][1,2,4]triazolo-[1,5-a]pyrimidine-7-amine |
| Q-13 | (1-25) N-[2-(1,3-dimethylbutyl)-3-thienyl]-2-methyl-4-(trifluoromethyl)-1,3-thiazole-5-carboxamide | (22-1) 5-chloro-N-[(1S)-2,2,2-trifluoro-1-methylethyl]-6-(2,4,6-trifluorophenyl)-[1,2,4]triazolo[1,5-a]pyrimidine-7-amine |
| Q-14 | (1-25) N-[2-(1,3-dimethylbutyl)-3-thienyl]-2-methyl-4-(trifluoromethyl)-1,3-thiazole-5-carboxamide | (22-2) 5-chloro-N-[(1R)-1,2-dimethylpropyl]-6-(2,4,6-trifluorophenyl)[1,2,4]triazolo-[1,5-a]pyrimidine-7-amine |
| Q-15 | (1-25) N-[2-(1,3-dimethylbutyl)-3-thienyl]-2-methyl-4-(trifluoromethyl)-1,3-thiazole-5-carboxamide | (22-4) 5-chloro-6-(2,4,6-trifluorophenyl)-7-(4-methylpiperidin-1-yl)[1,2,4]triazolo[1,5-a]-pyrimidine |
| Q-16 | (1-25) N-[2-(1,3-dimethylbutyl)-3-thienyl]-2-methyl-4-(trifluoromethyl)-1,3-thiazole-5-carboxamide | (22-5) 5-chloro-6-(2,4,6-trifluorophenyl)-N-[(1S)-1,2,2-trimethylpropyl][1,2,4]triazolo-[1,5-a]pyrimidine-7-amine |

Preference is given to active compound combinations R in which the iodochromone (group 23) is selected from the list below: (23-1) 2-butoxy-6-iodo-3-propylbenzopyran-4-one, (23-2) 2-ethoxy-6-iodo-3-propylbenzopyran-4-one, (23-3) 6-iodo-2-propoxy-3-propylbenzopyran-4-one, (23-4) 2-but-2-ynyloxy-6-iodo-3-propylbenzopyran-4-one, (23-5) 6-iodo-2-(1-methylbutoxy)-3-propylbenzopyran-4-one, (23-6) 2-but-3-enyloxy-6-iodobenzopyran-4-one, (23-7) 3-butyl-6-iodo-2-isopropoxybenzopyran-4-one.

Particular preference is given to active compound combinations T in which the iodochromone (group 23) is selected from the list below: (23-1) 2-butoxy-6-iodo-3-propylbenzopyran-4-one, (23-2) 2-ethoxy-6-iodo-3-propylbenzopyran-4-one.

Emphasis is given to the active compound combinations R listed in table 18 below:

TABLE 18

Active compound combinations R

| No. | Carboxamide of the formula (I) | Iodochromone of the formula (XV) |
|---|---|---|
| R-1 | (1-1) N-[2-(1,3-dimethylbutyl)-3-thienyl]-1-methyl-3-(trifluoromethyl)-1H-pyrazole-4-carboxamide | (23-1) 2-butoxy-6-iodo-3-propyl-benzopyran-4-one |
| R-2 | (1-1) N-[2-(1,3-dimethylbutyl)-3-thienyl]-1-methyl-3-(trifluoromethyl)-1H-pyrazole-4-carboxamide | (23-2) 2-ethoxy-6-iodo-3-propyl-benzopyran-4-one |
| R-3 | (1-9) N-[2-(1,3-dimethylbutyl)-3-thienyl]-5-fluoro-1,3-dimethyl-1H-pyrazole-4-carboxamide | (23-1) 2-butoxy-6-iodo-3-propyl-benzopyran-4-one |

TABLE 18-continued

Active compound combinations R

| No. | Carboxamide of the formula (I) | Iodochromone of the formula (XV) |
|---|---|---|
| R-4 | (1-9) N-[2-(1,3-dimethylbutyl)-3-thienyl]-5-fluoro-1,3-dimethyl-1H-pyrazole-4-carboxamide | (23-2) 2-ethoxy-6-iodo-3-propyl-benzopyran-4-one |
| R-5 | (1-13) N-[2-(1,3-dimethylbutyl)-3-thienyl]-1-methyl-4-(trifluoromethyl)-1H-pyrrole-3-carboxamide | (23-1) 2-butoxy-6-iodo-3-propyl-benzopyran-4-one |
| R-6 | (1-13) N-[2-(1,3-dimethylbutyl)-3-thienyl]-1-methyl-4-(trifluoromethyl)-1H-pyrrole-3-carboxamide | (23-2) 2-ethoxy-6-iodo-3-propyl-benzopyran-4-one |
| R-7 | (1-25) N-[2-(1,3-dimethylbutyl)-3-thienyl]-2-methyl-4-(trifluoromethyl)-1,3-thiazole-5-carboxamide | (23-1) 2-butoxy-6-iodo-3-propyl-benzopyran-4-one |
| R-8 | (1-25) N-[2-(1,3-dimethylbutyl)-3-thienyl]-2-methyl-4-(trifluoromethyl)-1,3-thiazole-5-carboxamide | (23-2) 2-ethoxy-6-iodo-3-propyl-benzopyran-4-one |

In addition to an active compound of the formula (I), the active compound combinations according to the invention comprise at least one active compound selected from the compounds of groups (2) to (23). In addition, they may also comprise further fungicidally active additives.

The synergistic effect is particularly pronounced when the active compounds in the active compound combinations according to the invention are present in certain weight ratios. However, the weight ratios of the active compounds in the active compound combinations can be varied within a relatively wide range. In general, the combinations according to the invention comprise active compounds of the formula (I) and a mixing partner of one of groups (2) to (23) in the mixing ratios given in an exemplary manner in table 19 below.

The mixing ratios are based on weight ratios. The ratio is to be understood as meaning active compound of formula (I): mixing partner.

TABLE 19

Mixing ratios

| Mixing partner | preferred mixing ratio | particularly preferred mixing ratio |
|---|---|---|
| Group (2): Strobilurins | 50:1 to 1:50 | 10:1 to 1:20 |
| Group (3): Triazoles | 50:1 to 1:50 | 20:1 to 1:20 |
| Group (4): Sulfenamides | 1:1 to 1:150 | 1:1 to 1:100 |
| Group (5): Valinamides | 50:1 to 1:50 | 10:1 to 1:20 |
| Group (6): Carboxamides | 50:1 to 1:50 | 20:1 to 1:20 |
| Group (7): Dithiocarbamates | 1:1 to 1:150 | 1:1 to 1:100 |
| Group (8): Acylalanines | 10:1 to 1:150 | 5:1 to 1:100 |
| Group (9): Anilinopyrimidines | 5:1 to 1:50 | 1:1 to 1:20 |
| Group (10): Benzimidazoles | 10:1 to 1:50 | 5:1 to 1:20 |
| Group (11): Carbamates | 1:1 to 1:150 | 1:1 to 1:100 |
| Group (12): (12-1)/(12-2) | 1:1 to 1:150 | 1:5 to 1:100 |
| Group (12): (12-3)/(12-4)/(12-5) | 5:1 to 1:50 | 1:1 to 1:20 |
| Group (13): Guanidines | 100:1 to 1:150 | 20:1 to 1:100 |
| Group (14): Imidazoles | 50:1 to 1:50 | 10:1 to 1:20 |
| Group (15): Morpholines | 50:1 to 1:50 | 10:1 to 1:20 |
| Group (16): Pyrroles | 50:1 to 1:50 | 10:1 to 1:20 |
| Group (17): Phosphonates | 10:1 to 1:150 | 1:1 to 1:100 |
| Group (18): Phenylethanamides | 50:1 to 1:50 | 10:1 to 1:20 |
| Group (19) | 50:1 to 1:150 | 20:1 to 1:100 |
| Group (20): (Thio)urea derivatives | 50:1 to 1:50 | 10:1 to 1:20 |
| Group (21): Amides | 50:1 to 1:50 | 10:1 to 1:20 |
| Group (22): Triazolopyrimidines | 50:1 to 1:50 | 10:1 to 1:20 |
| Group (23): Iodochromones | 50:1 to 1:50 | 10:1 to 1:20 |

In each case, the mixing ratio is to be chosen such that a synergistic mixture is obtained. The mixing ratios between the compound of the formula (I) and a compound of one of the groups (2) to (23) may also vary between the individual compounds of a group.

The active compound combinations according to the invention have very good fungicidal properties and can be used for controlling phytopathogenic fungi and bacteria.

In crop protection, fungicides can be used for controlling Plasmodiophoromycetes, Oomycetes, Chytridiomycetes, Zygomycetes, Ascomycetes, Basidiomycetes and Deuteromycetes.

In crop protection, bactericides can be used for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

Diseases caused by powdery mildew pathogens, such as, for example,

*Blumeria* species, such as, for example, *Blumeria graminis;*

*Podosphaera* species, such as, for example, *Podosphaera leucotricha;*

*Sphaerotheca* species, such as, for example, *Sphaerotheca fuliginea;*

*Uncinula* species, such as, for example, *Uncinula necator;*

Diseases caused by rust disease pathogens, such as, for example,

*Gymnosporangium* species, such as, for example, *Gymnosporangium sabinae*

*Hemileia* species, such as, for example, *Hemileia vastatrix;*

*Phakopsora* species, such as, for example, *Phakopsora pachyrhizi* and *Phakopsora meibomiae;*

*Puccinia* species, such as, for example, *Puccinia recondita;*

*Uromyces* species, such as, for example, *Uromyces appendiculatus;*

Diseases caused by pathogens from the group of the Oomycetes, such as, for example,

*Bremia* species, such as, for example, *Bremia lactucae;*

*Peronospora* species, such as, for example, *Peronospora pisi* or *P. brassicae;*

*Phytophthora* species, such as, for example *Phytophthora infestans;*

*Plasmopara* species, such as, for example, *Plasmopara viticola;*

*Pseudoperonospora* species, such as, for example, *Pseudoperonospora humuli* or *Pseudoperonospora cubensis;*

*Pythium* species, such as, for example, *Pythium ultimum;*

Leaf blotch diseases and leaf wilt diseases caused, for example, by

*Alternaria* species, such as, for example, *Alternaria solani;*

*Cercospora* species, such as, for example, *Cercospora beticola;*
*Cladiosporium* species, such as, for example, *Cladiosporium cucumerinum;*
*Cochliobolus* species, such as, for example, *Cochliobolus sativus*
(conidia form: *Drechslera*, Syn: *Helminthosporium*);
*Colletotrichum* species, such as, for example, *Colletotrichum lindemuthanium;*
*Cycloconium* species, such as, for example, *Cycloconium oleaginum;*
*Diaporthe* species, such as, for example, *Diaporthe citri;*
*Elsinoe* species, such as, for example, *Elsinoe fawcettii;*
*Gloeosporium* species, such as, for example, *Gloeosporium laeticolor;*
*Glomerella* species, such as, for example, *Glomerella cingulata;*
*Guignardia* species, such as, for example, *Guignardia bidwelli;*
*Leptosphaeria* species, such as, for example, *Leptosphaeria maculans;*
*Magnaporthe* species, such as, for example, *Magnaporthe grisea;*
*Mycosphaerella* species, such as, for example, *Mycosphaerelle graminicola;*
*Phaeosphaeria* species, such as, for example, *Phaeosphaeria nodorum;*
*Pyrenophora* species, such as, for example, *Pyrenophora teres;*
*Ramularia* species, such as, for example, *Ramularia collocygni;*
*Rhynchosporium* species, such as, for example, *Rhynchosporium secalis;*
*Septoria* species, such as, for example, *Septoria apii;*
*Typhula* species, such as, for example, *Typhula incarnata;*
*Venturia* species, such as, for example, *Venturia inaequalis;*
Root and stem diseases caused, for example, by
*Corticium* species, such as, for example, *Corticium graminearum;*
*Fusarium* species, such as, for example, *Fusarium oxysporum;*
*Gaeumannomyces* species, such as, for example, *Gaeumannomyces graminis;*
*Rhizoctonia* species, such as, for example *Rhizoctonia solani;*
*Tapesia* species, such as, for example, *Tapesia acuformis;*
*Thielaviopsis* species, such as, for example, *Thielaviopsis basicola;*
Ear and panicle diseases (including corn cobs) caused, for example, by
*Alternaria* species, such as, for example, *Alternaria* spp.;
*Aspergillus* species, such as, for example, *Aspergillus flavus;*
*Cladosporium* species, such as, for example, *Cladosporium* spp.;
*Claviceps* species, such as, for example, *Claviceps purpurea;*
*Fusarium* species, such as, for example, *Fusarium culmorum;*
*Gibberella* species, such as, for example, *Gibberella zeae;*
*Monographella* species, such as, for example, *Monographella nivalis;*
Diseases caused by smut fungi, such as, for example,
*Sphacelotheca* species, such as, for example, *Sphacelotheca reiliana;*
*Tilletia* species, such as, for example, *Tilletia caries;*
*Urocystis* species, such as, for example, *Urocystis occulta;*
*Ustilago* species, such as, for example, *Ustilago nuda;*
Fruit rot caused, for example, by
*Aspergillus* species, such as, for example, *Aspergillus flavus;*
*Botrytis* species, such as, for example, *Botrytis cinerea;*
*Penicillium* species, such as, for example, *Penicillium expansum;*
*Sclerotinia* species, such as, for example, *Sclerotinia sclerotiorum;*
*Verticilium* species, such as, for example, *Verticilium alboatrum;*
Seed- and soil-borne rot and wilt diseases, and also diseases of seedlings, caused, for example, by
*Fusarium* species, such as, for example, *Fusarium culmorum;*
*Phytophthora* species, such as, for example, *Phytophthora cactorum;*
*Pythium* species, such as, for example, *Pythium ultimum;*
*Rhizoctonia* species, such as, for example, *Rhizoctonia solani;*
*Sclerotium* species, such as, for example, *Sclerotium rolfsii;*
Cancerous diseases, galls and witches' broom caused, for example, by *Nectria* species, such as, for example, *Nectria galligena;*
Wilt diseases caused, for example, by
*Monilinia* species, such as, for example, *Monilinia laxa;*
Deformations of leaves, flowers and fruits caused, for example, by
*Taphrina* species, such as, for example, *Taphrina deformans;*
Degenerative diseases of woody plants caused, for example, by
*Esca* species, such as, for example, *Phaemoniella clamydospora;*
Diseases of flowers and seeds caused, for example, by
*Botrytis* species, such as, for example, *Botrytis cinerea;*
Diseases of plant tubers caused, for example, by
*Rhizoctonia* species, such as, for example, *Rhizoctonia solani;*
Diseases caused by bacteriopathogens, such as, for example,
*Xanthomonas* species, such as, for example, *Xanthomonas campestris* pv. *oryzae;*
*Pseudomonas* species, such as, for example, *Pseudomonas syringae* pv. *lachrymans;*
*Erwinia* species, such as, for example, *Erwinia amylovora.*
Preference is given to controlling the following diseases of soya beans:
fungal diseases on leaves, stems, pods and seeds caused, for example, by
alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi*), scab (*Sphaceloma glycines*), stemphylium leaf blight (*Stemphylium botryosum*), target spot (*Corynespora Cassiicola*)

Fungal diseases on roots and the stem base caused, for example, by black root rot (*Calonectria crotalariae*), charcoal rot (*Macrophomina phaseolina*), *fusarium* blight or wilt, root rot, and pod and collar rot (*Fusarium oxysporum, Fusarium orthoceras, Fusarium semitectum, Fusarium equiseti*), *mycoleptodiscus* root rot (*Mycoleptodiscus terrestris*), *neocosmospora* (*Neocosmopspora vasinfecta*), pod and stem blight (*Diaporthe phaseolorum*), stem canker (*Diaporthe phaseolorum* var. *caulivora*), *phytophthora* rot (*Phytophthora megasperma*), brown stem rot (*Phialophora gregata*), *pythium* rot (*Pythium aphanidermatum, Pythium irregulare, Pythium debaryanum, Pythium myriotylum, Pythium ultimum*), *rhizoctonia* root rot, stem decay, and damping-off (*Rhizoctonia solani*), *sclerotinia* stem decay (*Sclerotinia sclerotiorum*), *sclerotinia* Southern blight (*Sclerotinia rolfsii*), *thielaviopsis* root rot (*Thielaviopsis basicola*).

The fact that the active compound combinations are well tolerated by plants at the concentrations required for controlling plant diseases permits a treatment of entire plants (above-ground parts of plants and roots), of propagation stock and seed, and of the soil. The active compound combinations according to the invention can be used for foliar application or else as seed dressings.

The fact that the active compounds which can be used are well tolerated by plants at the concentrations required for controlling plant diseases permits a treatment of the seed. Accordingly, the active compounds according to the invention can be used as seed dressings.

A large part of the damage to crop plants which is caused by phytopathogenic fungi occurs as early as when the seed is attacked during storage and after the seed is introduced into the soil, as well as during and immediately after germination of the plants. This phase is particularly critical since the roots and shoots of the growing plant are particularly sensitive and even minor damage can lead to the death of the whole plant. Protecting the seed and the germinating plant by the use of suitable compositions is therefore of particularly great interest.

The control of phytopathogenic fungi which damage plants post-emergence is carried out primarily by treating the soil and the above-ground parts of plants with crop protection agents. Owing to the concerns regarding a possible impact of crop protection agents on the environment and the health of man and animals, there are efforts to reduce the amount of active compounds applied.

The control of phytopathogenic fungi by treating the seed of plants has been known for a long time and is subject-matter of continuous improvements. However, the treatment of seed entails a series of problems which cannot always be solved in a satisfactory manner. Thus, it is desirable to develop methods for protecting the seed and the germinating plant which dispense with the additional application of crop protection agents after sowing or after the emergence of the plants or where additional application is at least considerably reduced. It is furthermore desirable to optimize the amount of active compound employed in such a way as to provide maximum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection agents being employed.

The present invention therefore in particular also relates to a method for the protection of seed and germinating plants from attack by phytopathogenic fungi, by treating the seed with a composition according to the invention.

The invention likewise relates to the use of the compositions according to the invention for the treatment of seed for protecting the seed and the germinating plant from phytopathogenic fungi.

Furthermore, the invention relates to seed which has been treated with a composition according to the invention so as to afford protection from phytopathogenic fungi.

One of the advantages of the present invention is that, because of the particular systemic properties of the compositions according to the invention, treatment of the seed with these compositions not only protects the seed itself, but also the resulting plants after emergence, from phytopathogenic fungi. In this manner, the immediate treatment of the crop at the time of sowing or shortly thereafter can be dispensed with.

Furthermore, it must be considered as advantageous that the mixtures according to the invention can also be employed in particular in transgenic seed.

The compositions according to the invention are suitable for protecting seed of any plant variety which is employed in agriculture, in the greenhouse, in forests or in horticulture. In particular, this takes the form of seed of cereals (such as wheat, barley, rye, millet and oats), corn, cotton, soya beans, rice, potatoes, sunflowers, beans, coffee, beet (for example sugar beet and fodder beet), peanuts, vegetables (such as tomatoes, cucumbers, onions and lettuce), lawn and ornamental plants. The treatment of seed of cereals (such as wheat, barley, rye and oats), corn and rice is of particular importance.

In the context of the present invention, the composition according to the invention is applied to the seed either alone or in a suitable formulation. Preferably, the seed is treated in a state which is stable enough to avoid damage during treatment. In general, the seed may be treated at any point in time between harvest and sowing. The seed usually used has been separated from the plant and freed from cobs, shells, stalks, coats, hairs or the flesh of the fruit. Thus, for example, it is possible to use seed which has been harvested, cleaned and dried to a moisture content of below 15% by weight. Alternatively, it is also possible to use seed which, after drying, has, for example, been treated with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

The compositions according to the invention can be applied directly, that is to say without comprising further components and without having been diluted. In general, it is preferable to apply the composition to the seed in the form of a suitable formulation. Suitable formulations and methods for the treatment of seed are known to the skilled worker and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active compound combinations according to the invention are also suitable for increasing the yield of crops. In addition, they show reduced toxicity and are well tolerated by plants.

According to the invention, it is possible to treat all plants and parts of plants. Plants are to be understood here as meaning all plants and plant populations, such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes.

Parts of plants also include harvested material and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multilayer coating.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof, are treated. The term "parts" or "parts of plants" or "plant parts" has been explained above.

Particularly preferably, plants of the plant cultivars which are in each case commercially available or in use are treated according to the invention.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), corn, soya beans, potatoes, cotton, oilseed rape and also fruit plants (with the fruits apples, pears, citrus fruits and grapes), and particular emphasis is given to corn, soya beans, potatoes, cotton and oilseed rape. Traits that are emphasized are in particular increased defense of the plants against insects, by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are furthermore particularly emphasized are the increased tolerance of the plants to certain herbicidally active compounds, for example imidazolinones, sulfonylureas, glyphosate or phosphinotricin (for example the "PAT" gene). The genes which impart the desired traits in question can also be present in combination with one another in the transgenic plants. Examples of "Bt plants" which may be mentioned are corn varieties, cotton varieties, soya bean varieties and potato varieties which are sold under the trade names YIELD GARD® (for example corn, cotton, soya beans), KnockOut® (for example corn), Starlink® (eg corn), Bollgard® (cotton), Nucotn® (cotton) and NewLeaf® (potato). Examples of herbicide-tolerant plants which may be mentioned are corn varieties, cotton varieties and soya bean varieties which are sold under the trade names Roundup Ready® (tolerance to glyphosate, for example corn, cotton, soya beans), Liberty Link® (tolerance to phosphinotricin, for example oilseed rape), IMI® (tolerance to imidazolinones) and STS® (tolerance to sulfonylureas, for example corn). Herbicide-resistant plants (plants bred in a conventional manner for herbicide tolerance) which may be mentioned also include the varieties sold under the name Clearfield® (for example corn). Of course, these statements also apply to plant cultivars which have these genetic traits or genetic traits still to be developed, and which will be developed and/or marketed in the future.

Depending on their particular physical and/or chemical properties, the active compound combinations according to the invention can be converted into the customary formulations, such as solutions, emulsions, suspensions, powders, dusts, foams, pastes, soluble powders, granules, aerosols, suspoemulsion concentrates, natural and synthetic materials impregnated with active compound and microencapsulations in polymeric substances and in coating compositions for seed, and ULV cold and warm fogging formulations.

These formulations are produced in a known manner, for example by mixing the active compounds or active compound combinations with extenders, that is liquid solvents, liquefied gases under pressure, and/or solid carriers, optionally with the use of surfactants, that is emulsifiers and/or dispersants, and/or foam formers.

If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, or else water.

Liquefied gaseous extenders or carriers are to be understood as meaning liquids which are gaseous at standard temperature and under atmospheric pressure, for example aerosol propellants such as butane, propane, nitrogen and carbon dioxide.

Suitable solid carriers are: for example ammonium salts and ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, corn cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates, or else protein hydrolyzates. Suitable dispersants are: for example lignosulfite waste liquors and methylcellulose.

Tackifiers such as carboxymethylcellulose, natural and synthetic polymers in the form of powders, granules or latexes, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The active compound content of the use forms prepared from the commercial formulations may be varied within wide ranges. The concentration of active compound of the use forms for controlling animal pests, such as insects and acarids, may be from 0.0000001 to 95% by weight of active compound and is preferably from 0.0001 to 1% by weight. Application is in a customary manner adapted to the use forms.

The formulations for controlling unwanted phytopathogenic fungi generally comprise between 0.1 and 95% by weight of active compounds, preferably between 0.5 and 90%.

The active compound combinations according to the invention can be used as such, in the form of their formulations or as the use forms prepared therefrom, such as ready-to-use solutions, emulsifiable concentrates, emulsions, suspensions, wettable powders, soluble powders, dusts and granules. They are used in a customary manner, for example by watering (drenching), drip irrigation, spraying, atomizing, broadcasting, dusting, foaming, spreading-on, and as a powder for dry seed treatment, a solution for seed treatment, a water-soluble powder for seed treatment, a water-soluble powder for slurry treatment, or by encrusting etc.

The active compound combinations according to the invention can, in commercial formulations and in the use forms prepared from these formulations, be present as a mixture with other active compounds, such as insecticides, attractants, sterilants, bactericides, acaricides, nematicides, fungicides, growth regulators or herbicides.

When using the active compound combinations according to the invention, the application rates can be varied within a relatively wide range, depending on the kind of application. In the treatment of parts of plants, the application rates of active compound combination are generally between 0.1 and 10 000 g/ha, preferably between 10 and 1000 g/ha. In the treatment of seed, the application rates of active compound combination are generally between 0.001 and 50 g per kilogram of seed, preferably between 0.01 and 10 g per kilogram of seed. In the treatment of the soil, the application rates of active compound combination are generally between 0.1 and 10 000 g/ha, preferably between 1 and 5000 g/ha.

The active compound combinations can be used as such, in the form of concentrates or in the form of generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if desired desiccants and UV stabilizers, and, if desired, colorants and pigments and other processing auxiliaries.

The good fungicidal action of the active compound combinations according to the invention is demonstrated by the examples below. While the individual active compounds show weaknesses in their fungicidal action, the combinations show an action which exceeds a simple sum of actions.

A synergistic effect in the fungicides is always present when the fungicidal action of the active compound combinations exceeds the total of the action of the active compounds when applied individually.

The expected fungicidal action for a given combination of two active compounds can be calculated as follows, according to S. R. Colby ("Calculating Synergistic and Antagonistic Responses of Herbicide Combinations", Weeds 1967, 15, 20-22):

If

X is the efficacy when employing active compound A at an application rate of m g/ha, Y is the efficacy when employing active compound B at an application rate of n g/ha and E is the efficacy when employing active compounds A and B at application rates of m and n g/ha, $$\text{then } E = X + Y - \frac{X \times Y}{100}$$

Here, the efficacy is determined in %. 0% means an efficacy which corresponds to that of the control, whereas an efficacy of 100% means that no infection is observed.

If the actual fungicidal action exceeds the calculated value, the action of the combination is superadditive, i.e. a synergistic effect is present. In this case, the actually observed efficacy must exceed the value calculated using the above formula for the expected efficacy (E).

USE EXAMPLES

Example A

*Puccinia* Test (Wheat)/Protective

Solvent: 50 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier or a commercial active compound formulation, and the concentrate is diluted with water to the desired concentration.

To test for protective activity, young plants are sprayed with the preparation of active compound at the stated application rate. After the spray coating has dried on, the plants are sprayed with a conidia suspension of *Puccinia recondita*. The plants remain in an incubation cabin at 20° C. and 100% relative atmospheric humidity for 48 hours.

The plants are then placed in a greenhouse at a temperature of about 20° C. and a relative atmospheric humidity of 80% to promote the development of rust postules.

Evaluation is carried out 10 days after the inoculation. 0% means inefficacy which corresponds to that of the control, whereas an efficacy of 100% means that no infection is observed.

amounts of solvent and emulsifier or a commercial active compound formulation, and the concentrate is diluted with water to the desired concentration.

To test for protective activity, young plants are sprayed with the preparation of active compound at the stated application rate.

TABLE A

Puccinia test (wheat) protective

| Active compounds | | Active compound application rate in g/ha | Efficacy in % found* | calc.** |
|---|---|---|---|---|
| (1-1) N-[2-(1,3-dimethylbutyl)-3-thienyl]-1-methyl-3-(trifluoromethyl)-1H-pyrazole-4-carboxamide | | 250 | 67 | |
| (1-1) N-[2-(1,3-dimethylbutyl)-3-thienyl]-1-methyl-3-(trifluoromethyl)-1H-pyrazole-4-carboxamide | | 125 | 33 | |
| (2-9) picoxystrobin | | 250 | 94 | |
| (3-6) cyproconazole | | 125 | 94 | |
| (9-1) cyprodinil | | 125 | 0 | |
| (3-7) hexaconazole | | 125 | 78 | |
| (3-3) propiconazole | | 125 | 56 | |
| (1-1) + (2-9) picoxystrobin 1:1 | (A-5) | 250 + 250 | 100 | 98 |
| (1-1) + (3-6) cyproconazole 1:1 | (B-3) | 125 + 125 | 100 | 96 |
| (1-1) + (9-1) cyprodinil 1:1 | (H-1) | 125 + 125 | 44 | 33 |
| (1-1) + (3-7) hexaconazole 1:1 | (B-4) | 125 + 125 | 100 | 85 |
| (1-1) + (3-3) propiconazole 1:1 | (B-1) | 125 + 125 | 78 | 70 |

*found = activity found
**calc. = activity calculated using Colby's formula

Example B

Erysiphe Test (Wheat)/Protective

| Solvent: | 50 parts by weight of N,N-dimethylacetamide |
|---|---|
| Emulsifier: | 1 part by weight of alkylarylpolyglycol ether |

To produce a suitable preparation of active compound, 1 part by weight of active compound is mixed with the stated After the spray coating has dried on, the plants are dusted with spores of Erysiphe graminis f. sp. tritici.

The plants are placed in a greenhouse at a temperature of about 20° C. and a relative atmospheric humidity of about 80% to promote the development of mildew pustules.

Evaluation is carried out 7 days after the inoculation. 0% means an efficacy which corresponds to that of the control, whereas an efficacy of 100% means that no infection is observed.

TABLE B

Erysiphe test (wheat) protective

| Active compound | | Active compound application rate in g/ha | Efficacy in % found* | calc.** |
|---|---|---|---|---|
| (1-1) N-[2-(1,3-dimethylbutyl)-3-thienyl]-1-methyl-3-(trifluoromethyl)-1H-pyrazol-4-carboxamide | | 62.5 | 0 | |
| (2-9) picoxystrobin | | 62.5 | 71 | |
| (3-6) cyproconazole | | 62.5 | 57 | |
| (9-1) cyprodinil | | 62.5 | 0 | |
| (3-7) hexaconazole | | 62.5 | 29 | |
| (3-3) propiconazole | | 62.5 | 29 | |
| (1-1) + (2-9) picoxystrobin 1:1 | (A-5) | 62.5 + 62.5 | 86 | 71 |
| (1-1) + (3-6) cyproconazole 1:1 | (B-3) | 62.5 + 62.5 | 93 | 57 |
| (1-1) + (9-1) cyprodinil 1:1 | (H-1) | 62.5 + 62.5 | 29 | 0 |
| (1-1) + (3-7) hexaconazole 1:1 | (B-4) | 62.5 + 62.5 | 57 | 29 |
| (1-1) + (3-3) propiconazole 1:1 | (B-1) | 62.5 + 62.5 | 57 | 29 |

*found = activity found
**calc. = activity calculated using Colby's formula

The invention claimed is:

1. An active compound combination consisting of (1-1) penthiopyrad, one azole selected from the group consisting of: (3-3) propiconazole, (3-4) difenoconazole, (3-6) cyproconazole, (3-7) hexaconazole, (3-8) penconazole, and (3-17) tebuconazole, and optionally an extender, a surfactant, or a combination thereof, wherein the ratio of (1-1) penthiopyrad to the azole is from 50:1 to 1:50, and wherein said (1-1) penthiopyrad and azole are present in synergistic amounts.

2. The active compound combination according to claim 1, wherein the azole is (3-3) propiconazole.

3. The active compound combination according to claim 2, wherein the ratio of (1-1) penthiopyrad to (3-3) propiconazole is from 20:1 to 1:20.

4. The active compound combination according to claim 3, wherein the ratio of (1-1) penthiopyrad to (3-3) propiconazole is 1:1.

5. The active compound combination according to claim 1, wherein the azole is (3-4) difenoconazole.

6. The active compound combination according to claim 5, wherein the ratio of (1-1) penthiopyrad to (3-4) difenoconazole is from 20:1 to 1:20.

7. The active compound combination according to claim 1, wherein the azole is (3-6) cyproconazole.

8. The active compound combination according to claim 7, wherein the ratio of (1-1) penthiopyrad to (3-6) cyproconazole is from 20:1 to 1:20.

9. The active compound combination according to claim 8, wherein the ratio of (1-1) penthiopyrad to (3-6) cyproconazole is 1:1.

10. The active compound combination according to claim 1, wherein the azole is (3-7) hexaconazole.

11. The active compound combination according to claim 10, wherein the ratio of (1-1) penthiopyrad to (3-7) hexaconazole is from 20:1 to 1:20.

12. The active compound combination according to claim 11, wherein the ratio of (1-1) penthiopyrad to (3-7) hexaconazole is 1:1.

13. The active compound combination according to claim 1, wherein the azole is (3-8) penconazole.

14. The active compound combination according to claim 13, wherein the ratio of (1-1) penthiopyrad to (3-8) penconazole is from 20:1 to 1:20.

15. The active compound combination according to claim 1, wherein the azole is (3-17) tebuconazole.

16. The active compound combination according to claim 15, wherein the ratio of (1-1) penthiopyrad to (3-17) tebuconazole is from 20:1 to 1:20.

17. A seed treated with the active compound combination according to claim 1.

18. A method for controlling unwanted phytopathogenic fungi, or treating seeds or transgenic plants comprising contacting said fungi, seeds, transgenic plants or their habitat with an active compound combination consisting of (1-1) penthiopyrad, one azole selected from the group consisting of (3-3) propiconazole, (3-4) difenoconazole, (3-6) cyproconazole, (3-7) hexaconazole, (3-8) penconazole, and (3-17) tebuconazole, and optionally an extender, a surfactant, or a combination thereof, wherein the ratio of (1-1) penthiopyrad to the azole is from 50:1 to 1:50, and wherein said (1-1) penthiopyrad and azole are present in synergistic amounts.

19. The method according to claim 18, wherein said fungi are rust disease pathogens.

20. The method according to claim 19, wherein said rust disease pathogens are *Puccinia* species.

21. The method according to claim 18, wherein said *Puccinia* species are *Puccinia recondita*.

22. The method according to claim 18, wherein said fungi are *Erysiphe graminis* f.sp. *tritici*.

23. The method according to claim 18, wherein said fungi are *Alternaria* species.

24. The method according to claim 23, wherein said *Alternaria* species are *Alternaria solani*.

25. The method according to claim 18, wherein said fungi are *Sphaerotheca* species.

26. The method according to claim 25, wherein said *Sphaerotheca* species are *Sphaerotheca fuliginea*.

27. The method according to claim 18, wherein said fungi are *Venturia* species.

28. The method according to claim 27, wherein said *Venturia* species are *Venturia inaequalis*.

29. The method according to claim 18, wherein said fungi are *Septoria* species.

* * * * *